United States Patent [19]

Harris et al.

[11] 4,415,496
[45] Nov. 15, 1983

[54] BICYCLIC LACTAMS

[75] Inventors: Elbert E. Harris; Arthur A. Patchett, both of Westfield; Edward W. Tristram, Watchung; Eugene D. Thorsett, Fanwood; Matthew J. Wyvratt, Jr., Mountainside, all of N.J.

[73] Assignee: Merck & Co., Inc., Rahway, N.J.

[21] Appl. No.: 348,811

[22] Filed: Feb. 19, 1982

Related U.S. Application Data

[63] Continuation-in-part of Ser. No. 246,492, Mar. 23, 1981, abandoned.

[51] Int. Cl.³ .......................................... C07D 513/04

[52] U.S. Cl. ............................. 260/239.3 B; 424/258; 424/263; 424/270
[58] Field of Search .................. 260/239.3 B; 424/270, 424/258, 263

[56] References Cited

U.S. PATENT DOCUMENTS 4,192,945 3/1980 Ondetti ................................. 546/245
4,225,495 9/1980 Ondetti ............................. 260/244.4

Primary Examiner—Robert T. Bond
Attorney, Agent, or Firm—Salvatore C. Mitri; Rudolph J. Anderson

[57] ABSTRACT

The invention relates to bicyclic lactams and related compounds which are useful as antihypertensives.

29 Claims, No Drawings

BICYCLIC LACTAMS

BACKGROUND OF INVENTION

This application is a continuation-in-part of application Ser. No. 246,492 filed Mar. 23, 1981, now abandoned.

The invention in its broad aspects relates to bicyclic lactams and derivatives thereof which are useful as converting enzyme inhibitors and as antihypertensives. The compounds of this invention are represented by the following formula:

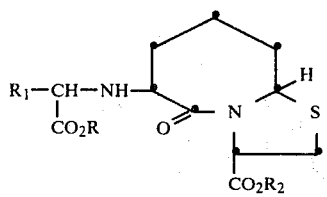

wherein:

R and $R_2$ are independently hydrogen, loweralkyl, aryl, and aralkyl;

$R_1$ is hydrogen;

alkyl of from 1 to 12 carbon atoms which include branched, cyclic and unsaturated alkyl groups (such as 3-methyl-1-butyl, 2-cyclohexylethyl, 3,3-dimethylallyl, and the like);

substituted lower alkyl wherein the substituent can be halo, hydroxy, carboxy, lower alkylthio, lower alkoxy, lower alkoxy carbonyl, lower aralkoxy carbonyl, amino, lower alkylamino, lower dialkylamino, or acylamino;

substituted lower alkyl having the formula $R_A(CH_2)_n$—Q—$(CH_2)_m$ wherein n is 0–2, m is 1–3, $R_A$ is aryl or heteroaryl optionally substituted by amino, lower dialkylamino, lower alkylamino, hydroxy, hydroxy loweralkyl, aminoloweralkyl, trihaloloweralkyl, cyano, nitro, sulfonamido, aroyl, lower alkyl, halo, dihalo, and lower alkoxy, and Q is O, S, N—$R_B$, CONR_C, NR_CCO, CH=CH wherein $R_B$ is hydrogen, loweralkyl, aryl, aralkyl, lower alkanoyl, or aroyl, and $R_C$ is hydrogen or lower alkyl;

aryl (such as phenyl, naphthyl or biphenyl);

substituted aryl wherein the substituent is lower alkyl, amino loweralkyl, loweralkoxy, aryloxy, aroyl, hydroxy, halo, or dihalo; aralkyl or heteroaralkyl which include branched lower alkyl groups (such as 2,2-dibenzylethyl);

substituted aralkyl or substituted heteroaralkyl which include branched lower alkyl groups wherein the lower alkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, amino lower alkyl, lower alkanoylamino, aroylamino, lower dialkylamino, lower alkylamino, hydroxy, hydroxy loweralkyl, trihalo loweralkyl, nitro, cyano, or sulfonamido; and, the pharmaceutically acceptable salts thereof.

The lower alkyl groups, except where noted otherwise, represented by any of the variables include straight, branched and unsaturated chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like. The aralkyl and heteroaralkyl groups represented by any of the above variables have from one to six carbon atoms in the alkyl portion thereof and include for example, benzyl, phenethyl, 3,3-diphenylpropyl, 3-indolylmethyl, and the like. Halo means chloro, bromo, iodo or fluoro. Aryl where it appears in any of the radicals, except where noted, represents phenyl, naphthyl, or biphenyl. Aroyl includes benzoyl, 1-naphthyl, and the like. Heteroaryl includes, for example, indolyl, thienyl, imidazolyl, furyl, benzimidazolyl, pyridyl, quinolinyl, isoquinolinyl, and benzothienyl. Acylamino refers to lower alkanoylamino and aroylamino groups such as, for example, acetylamino, benzoylamino, and the like.

Preferred are those compounds of Formula I wherein:

R and $R_2$ are hydrogen, loweralkyl, aryl or aralkyl; and, $R_1$ is alkyl of 1–10 carbon atoms which include branched, cyclic and unsaturated alkyl groups;

substituted loweralkyl wherein the substituent can be hydroxy, lower alkylthio, amino, alkylamino, lower dialkylamino, and acylamino;

substituted lower alkyl having the formula $R_A(CH_2)_n$—Q—$(CH_2)_m$— wherein n is 0–2, m is 1–3, $R_A$ is aryl or heteroaryl optionally substituted by alkyl, halo, dihalo, amino, cyano, hydroxy, or alkoxy, and Q is O, S, N—$R_B$, CONR_C, NR_CCO, or CH=CH wherein $R_B$ is hydrogen, lower alkyl, aralkyl, lower alkanoyl, or aroyl and $R_C$ is hydrogen or lower alkyl;

aralkyl or heteroaralkyl which include branched lower alkyl groups; substituted aralkyl or substituted heteroaralkyl which include branched lower alkyl groups wherein the lower alkyl substituents can be amino, acylamino, or hydroxy and the aryl and heteroaryl substituents can be lower alkyl, halo, dihalo, amino, cyano, hydroxy, lower alkoxy, amino loweralkyl, or hydroxyloweralkyl.

Still more preferred are those compounds of Formula I wherein:

R and $R_2$ are independently hydrogen, loweralkyl, aryl, or aralkyl; and, $R_1$ is alkyl of 1–10 carbon atoms which include branched alkyl groups;

substituted lower alkyl wherein the substituent can be amino, acylamino, or lower alkylthio;

substituted lower alkyl having the formula $R_A(CH_2)_n$—Q—$(CH_2)_m$— wherein n is 0–1, m is 1–2, $R_A$ is phenyl optionally substituted by halo, dihalo, alkoxy, or cyano, and Q is O or S; aralkyl or heteroaralkyl;

substituted aralkyl or substituted heteroaralkyl wherein the aryl and heteroaryl substituents are halo, dihalo, cyano, hydroxy, hydroxy lower alkyl, amino, and amino lower alkyl.

Most preferred are compounds of Formula I wherein:

R and $R_2$ are independently hydrogen, lower alkyl of 1 to 4 carbon atoms, phenyl, or benzyl; and, $R_1$ is alkyl of 1–8 carbon atoms which include branched alkyl groups;

substituted lower alkyl wherein the substituent can be amino or loweralkylthio; substituted lower alkyl having the formula $R_A(CH_2)_n$—Q—$(CH_2)_m$— wherein n is O, m is 1, $R_A$ is phenyl, and Q is O or S;

aralkyl wherein the aryl is phenyl or naphthyl and the alkyl group contains 1 to 3 carbon atoms, or heteroaralkyl wherein the heteroaryl group is indole, thiophene, imidazole, pyridine, quinoline or isoquinoline and the alkyl group contains 1 to 3 carbon atoms;

substituted aralkyl wherein the aryl is a phenyl group, the alkyl contains 1 to 3 carbon atoms, and the phenyl substituents can be halo, hydroxy, phenoxy, lower alkoxy, amino, or aminomethyl.

The preferred, more preferred and most preferred compounds also include the pharmaceutically acceptable salts thereof.

The products of Formula (I) can be produced from bicyclic intermediate VIII and from the separated, preferred diastereomers of VIII; i.e., VIIIa and VIIIb. The synthesis of compound VIII can be conducted from, for example, 2(S)-amino-6-hydroxyhexanoic acid II as shown in Reaction Scheme I below wherein $R_2$ is as defined above.

REACTION SCHEME I

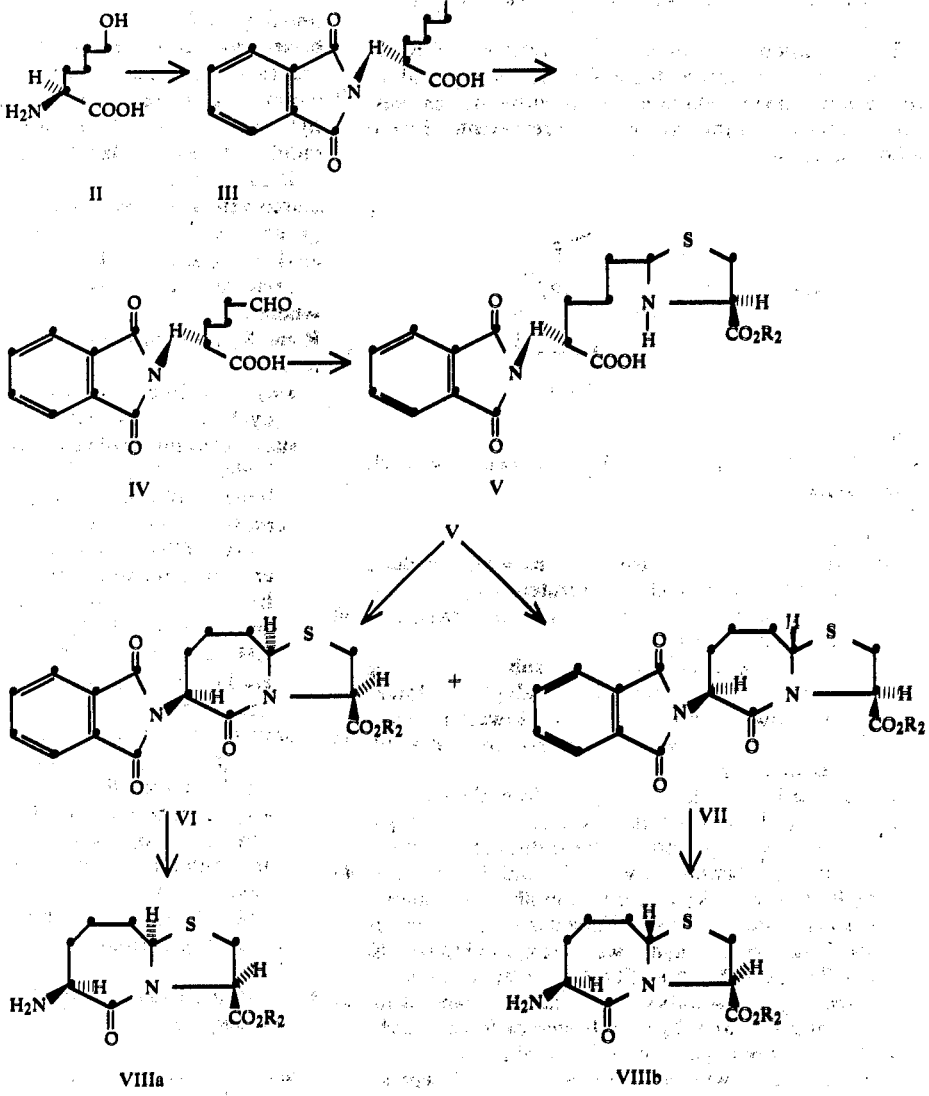

As shown in Reaction Scheme I above, known starting material II is protected as the phthalimido derivative III and oxidized with pyridinium dichromate to the aldehyde, 5-formyl-2(S)-phthalimidopentanoic acid IV. Condensation with an ester of R-cysteine yields a diastereomeric mixture of thiazolidines V which, upon treatment with N-ethoxycarbonyl-2-ethoxy-1,2-dihydroquinoline, undergo ring closure to form S, R, R(VI) and S, S, R(VII) methyl 6-phthalimidooctahydro-5-oxothiazolo[3,2-a]azepine-3-carboxylate. The isomers are separated by liquid chromatography and are deprotected by treatment with hydrazine to yield aminoesters VIIIa and VIIIb. The ester group can then be removed with dilute alkali to yield the acids ($R_2$=H) of VIIIa and VIIIb.

As summarized in Reaction Scheme II below, products of Formula I can be prepared from the diastereomeric mixture of amino cyclic lactams VIII or from diastereomerically pure compounds VIIIa and VIIIb by reductive alkylation of these intermediates with α-keto acids or α-keto esters IX. In these alkylations, one typically uses sodium cyanoborohydride under neutral conditions, but it is also possible to employ hydrides bearing optically active ligands or sterically bulky ligands selected to improve the sterochemical control in these reductions. Alternatively, the reductive alkylations can be achieved by catalytic hydrogenation over 10% palladium on carbon or other suitable catalysts.

The final stages in these syntheses are to separate the desired diastereomers by chromatography or crystallization and to remove protecting groups, if present, by standard means. When identical diesters of Formula I are desired, they can be prepared from, for example, diacids of $I(R=R_2=H)$ using the desired alcohols under anhydrous acidic conditions.

REACTION SCHEME II

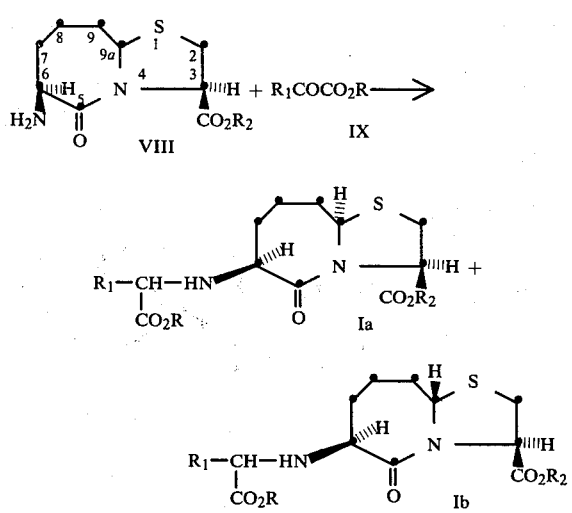

In Reaction Scheme III which follows, an alternate route to compounds of Formula I is shown which involves a variation in the sequence of the reactions utilized in Reaction Schemes I and II. In Reaction Scheme III, the reductive alkylation using IX is performed on intermediate X followed by ring closure of intermediate XII to yield products of Formula I after chromatography and removal of protecting groups. In this sequence, R, $R_1$ and $R_2$ are as defined above (except R, $R_2 \neq H$) and Z is optionally hydrogen or a suitable protecting functionality such as, for example, the formyl group. The ring forming and reductive alkylation reactions are performed under substantially the same conditions as utilized in and described above for Reaction Schemes I and II.

REACTION SCHEME III

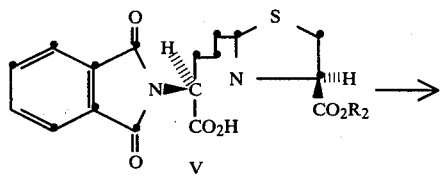

-continued
REACTION SCHEME III

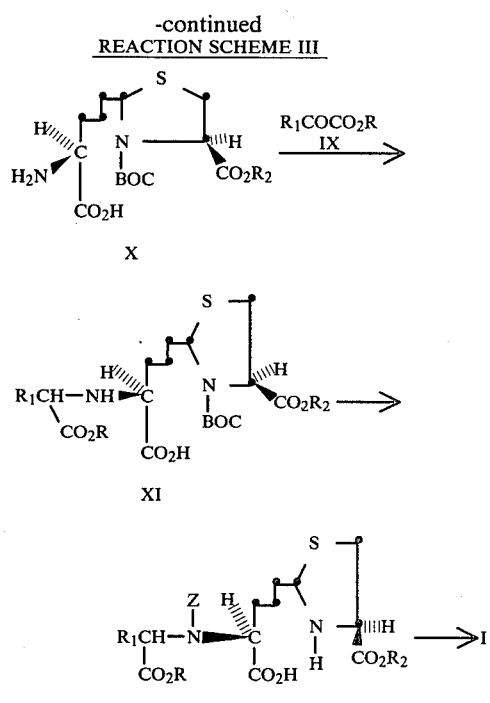

Intermediate VIII has three asymmetric carbon atoms: one bears the $NH_2$ group; another is that bearing the hydrogen at the ring juncture; and, a third is that bearing the $CO_2R_2$ group. The preferred absolute configuration at these centers are 6(S), 9a(R), 3(R) (VIIIa) and 6(S), 9a(S), 3(R) (VIIIb).

In Formula I compounds, the carbon atom bearing $R_1$ is also asymmetric ($R_1 \neq H$). Both isomers in this position have some biological activity, although the natural L-aminoacid configuration is preferred. In most cases, the absolute configuration at this center is designated (S).

Preferred diastereomers are isolated by chromatography or crystallization of intermediates or the end products or their salts. One can also resolve intermediates by the use of optically active salts or bases. Finally, if desired, compounds of this invention can also be employed as a mixture of their enantiomers or diastereomers.

The α-keto acids and α-keto esters IX utilized in the process of the invention are known in the art or can be made by numerous, known methods. For example, synthons such as

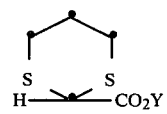

can be converted to α-keto acids or esters using methods involving alkylation followed by hydrolysis as described in the literature. An excellent method involves the reaction of Grignard reagents $R_1MgX$ with $ClCOCO_2Y$ or $YO_2CCO_2Y$. Another method involves condensing substituted acetic acid esters with diethyl oxalate followed by hydrolytic decarboxylation under acidic conditions to obtain α-keto acids. Carefully controlled acid hydrolysis in alcohol of acyl cyanides, which are prepared from acid chlorides and cuprous cyanide, also proves to be a viable synthetic route to α-keto esters. Nucleophilic displacement reactions on chloro or bromo pyvuric acid (ester) can also be used to produce a variety of interesting α-keto acids (esters). In these formulae, Y is a group such as loweralkyl or benzyl and protecting groups are employed as necessary in the $R_1$ group if interfering functionality is present.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Also salts with organic and inorganic acids may be prepared, e.g., HCl, HBr, $H_2SO_4$, $H_3PO_4$, methanesulfonic, toluenesulfonic, maleic, fumaric, camphorsulfonic. The non-toxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus, blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.* 125, 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 0.5 to 100 mg per patient generally given several times, thus giving a total daily dose of from 0.5 to 400 mg per day. The dose will vary depending on severity of diseases, weight of patient and other factors which a person skilled in the art will recognize.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, ethacrynic acid, furosemide, quanethidene sulfate, hydralazine hydrochloride, hydrochlorothiazide, hydroflumethiazide, metolazone, metoprolol tartate, methylclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivaloyloxyethyl ester of methyldopa, indacrinone and variable ratios of its enantiomers, nifedipine, verapamil, diltiazam, flumethiazide, bendroflumethiazide, atenolol, (+)-4-{3-{-[2-(1-hydroxycyclohexyl)ethyl]-4-oxo-2-thiazolidinyl}propyl} benzoic acid, bumetanide, prazosin, propranolol, rauwolfia serpentina, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 0.5–100 milligrams per day range can be effectively combined at levels at the 0.1–100 milligrams per day range with the following compounds at the indicated per day dose range: hydrochlorothiazide (10–100 mg), timolol (5–60 mg), methyldopa (65–2000 mg), the pivaloyloxyethyl ester of methyldopa (30–1000 mg), indacrinone and variable ratios of its enantiomers (25–150 mg) and (+)-4-{3-{[2-(1-hydroxycyclohexyl)ethyl]-4-oxo-2-thiazolidinyl}propyl}-benzoic acid (10–100 mg).

In addition, the triple drug combinations of hydrochlorothiazide (10–100 mg) plus timolol (5–60 mg) plus converting enzyme inhibitor of this invention (0.5–100 mg) or hydrochlorothiazide (10–100 mg) plus amiloride (5–20 mg) plus converting enzyme inhibitor of this invention (0.5–100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, the combinations shown above are formulated into pharmaceutical compositions as discussed below.

About 0.1 to 50 mg of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules, and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by conventional column chromatography or fractional crystallization. Unless otherwise indicated, all temperatures are in degrees Celsius.

EXAMPLE 1

6-Hydroxy-2(S)-phthalimidohexanoic Acid

Sodium carbonate (4.82 g) and 2(S)-amino-6-hydroxyhexanoic acid (6.70 g) were dissolved in 70 ml of water and treated with 9.98 g of N-carbethoxyphthalimide. The mixture was stirred for 1.5 hours and then filtered to remove unreacted N-carbethoxyphthalimide. The filtrate was cooled and acidified with 6 N HCl. The white precipitate (10.6 g) was isolated by filtration and recrystallized from water to give fine needles, m.p. 162–163; $[\alpha]_D^{25°} = -36.3°$ (MeOH, c=2.0). Tlc on silica (4:1 ethyl acetate:acetic acid) indicated a single spot, $R_f=0.67$. The $^1$H NMR spectrum (d$_6$-DMSO) showed a singlet at $\delta 7.90$ (4H), triplets at $\delta 4.77$ (1H, J=7.9 Hz) and $\delta 3.36$ (2H, J=6.0 Hz), and multiplets centered at 2.15 (2H) and 1.40 (4H).

Anal. Calcd. for $C_{14}H_{15}NO_5$: C, 60.64; H, 5.46; N, 5.05. Found: C, 60.69; H, 5.44; N, 4.97.

EXAMPLE 2

5-Formyl-2(S)-phthalimidopentanoic acid

6-Hydroxy-2(S)-phthalimidohexanoic acid (1.94 g) was dissolved in 145 ml of CH$_2$Cl$_2$ containing 2.26 ml of pyridine. Pyridinium dichromate (1.95 g) was added and the mixture stirred overnight under nitrogen. By addition to 200 ml of ethyl acetate and filtration, chromium salts were removed. The filtrate was concentrated under vacuum. The residue was redissolved in 250 ml of ethyl acetate and the solution refiltered. The filtrate was finally passed through a MgSO$_4$ pad to remove trace amounts of chromium salts and concentrated to afford a white solid, 0.475 g; m.p. 219°–22°; $[\alpha]_D^{25°} = -41.6°$ (THF, c=1.5). Tlc on silica (4:1 ethyl acetate:acetic acid) indicated a single spot at $R_f=0.79$. $^1$H NMR spectrum (d$_6$-DMSO) showed triplets at $\delta 9.65$ (1H) and $\delta 4.85$ (1H, J=7.5 Hz), a singlet at $\delta 7.95$ (4H), and a broad multiplet at $\delta 0.9$–2.50 (6H) ppm. $^{13}$C NMR spectrum (d$_6$-DMSO) showed single absorptions at 202.9, 170.5, 167.5, 134.9, 131.3, 123.5, 51.7, 42.4, 27.8, and 18.7 ppm.

Anal. Calcd. for $C_{14}H_{13}NO_5$: C, 61.09, H, 4.76; N, 5.09. Found: C, 60.93; H, 5.05; N, 5.39.

EXAMPLE 3

Alternative Synthesis of 5-Formyl-2(S)-phthalimidopentanoic acid

6-Hydroxy-2(S)-phthalimidohexanoic acid (5.0 g) was dissolved in a mixture of 90 ml of methanol and 9 ml of water. To this solution, an aqueous 0.5 M cesium carbonate solution (18 ml) was added and the mixture stirred for a few minutes. Most of the methanol was removed in vacuo and the resulting aqueous residue was freeze-dried. The lyophilized material was dissolved in DMF (70 ml) and treated with 3.08 g of benzyl bromide. After stirring under nitrogen for 6 hours, the reaction mixture was diluted with 450 ml of water and repeatedly extracted with ethyl acetate. Organic layers were then back-washed with water, dried (Na$_2$SO$_4$), and concentrated to give 6.58 g of benzyl 6-hydroxy-2(S)-phthalimidohexanoate. Recrystallization from ether gave a white solid, m.p. 106.5°–108°; $[\alpha]_D^{25°} = -27.6°$ (MeOH, c=1.77).

Benzyl 6-hydroxy-2(S)-phthalimidohexanoate (4.0 g) was dissolved in CH$_2$Cl$_2$ and treated with pyridinium chlorochromate (3.64 g). The reaction mixture was stirred under nitrogen for 4 hours and then diluted with 160 ml of ether. The mixture was filtered through a celite pad and concentrated to give an oil. This oil was passed through a short florisil column with ether as eluent. Concentration and drying in vacuo yielded pure benzyl 5-formyl-2(S)-phthalimidopentanoate (3.16 g); $[\alpha]_D^{25°} = -18.6°$ (CH$_2$Cl$_2$, c=4.1); I.R. (neat): 2730 cm$^{-1}$.

Benzyl 5-formyl-2(S)-phthalimidopentanoate (4.72 g) was dissolved in 230 ml of ethyl acetate and hydrogenated at 5 psig of hydrogen over 0.82 g of 10% palladium on carbon. After the uptake of 1 equivalent of hydrogen, catalyst was removed by filtration. Removal of solvent afforded 3.64 g of 5-formyl-2(S)-phthalimidopentanoic acid.

EXAMPLE 4

Methyl 2-(4'-carboxy-4'-phthalimidobutyl)-4(R)-thiazolidinecarboxylate

A solution of L-cysteine methyl ester (1.71 g) and 5-formyl-2(S)-phthalimidopentanoic acid (3.49 g) in 120 ml of tetrahydrofuran was stirred under nitrogen for 2.5 hours and then taken to dryness to yield a white foam. This residue was dissolved in 250 ml of chloroform and washed with water (2×30 ml). The combined aqueous layers were back extracted with chloroform (2×30 ml). The organic layers were dried (Na$_2$SO$_4$) and then concentrated in vacuo to give a white foam, 4.83 g. Tlc on silica [4:1 Ethyl acetate:acetic acid] indicated a major spot at $R_f=0.72$. Exact mass measurement showed a molecular ion at 392.1024 (calcd. 392.1041). $^1$H NMR spectrum (CDCl₃) showed a multiplet at δ7.72 (4H) and a singlet at δ3.78(3H).

Anal. Calcd. for $C_{18}H_{20}N_2O_6S\cdot\frac{1}{2}H_2O$: C, 53.85; H, 5.27; N, 6.98; S, 7.99. Found: C, 54.00; H, 5.30; N, 6.58; S, 7.61.

EXAMPLE 5

Methyl [3R-(3α,6α,9aα)]-6-phthalimidooctahydro-5-oxo-thiazolo[3,2-a]azepine-3-carboxylate and methyl [3R-(3α,6α,9aβ)]-6-phthalimidooctahydro-5-oxo-thiazolo[3,2-a]azepine-3-carboxylate The mixture of diastereomeric thiazolidines (677 mg) obtained in Example 4 and 469 mg of N-ethoxycarbonyl-2-ethoxy-1,2-dihydroquinoline (EEDQ) were dissolved in 30 ml of tetrahydrofuran and stirred at room temperature overnight under nitrogen. Concentration afforded a clear residue which was dissolved in 175 ml of ethyl acetate and washed with dilute hydrochloric acid (0.5 N), 5% sodium bicarbonate solution, water, and brine. The residue, after drying with Na₂SO₄, was chromatographed on silica gel (eluant 1:1 ethyl acetate:-hexane) to afford a mixture of isomers, wt. 348 mg. The diastereomers were separated on a Whatman ODS-3 reverse phase column using a 70:30 water-acetonitrile mixture as eluant.

The first component eluted from the column was methyl [3R-(3α,6α,9aα)]-6-phthalimidooctahydro-5-oxothiazolo-[3,2-a]azepine-3-carboxylate (9a(S) isomer), 141 mg. Recrystallization from ethyl acetate/hexane afforded fine white needles, m.p. 159.5°–61°; $[\alpha]_D^{25} = -202.1$ (CHCl₃); 300 MHz ¹H NMR(CDCl₃) δ1.99 (m, 3H), 2.29 (m, 2H), 2.94 (m, 1H), 3.27 (½ABq, $J_{AB}=12$ Hz, $\Delta V_{AB}=34$, $J_{AX}=7$ Hz, 1H), 3.16 (½ABq, $J_{AB}=12$ Hz, $\Delta V_{AB}=34$, $J_{BX}=7$ Hz, 1H), 3.75 (s, 3H), 5.01 (d, J=12 Hz, 1H), 5.21 (t, J=7 Hz, 1H), 5.27 (dd, J=9.5 Hz, J=4 Hz, 1H), 7.75 (m, 2H), 7.88 (m, 2H); I.R. (KBr): 1710 and 1650 cm⁻¹.

Anal. Calcd. for $C_{18}H_{18}N_2O_5S$: C, 57.74; H, 4.84; N, 7.48; S, 8.57. Found: C, 57.70; H, 4.87; N, 7.41; S, 8.45.

The second component eluted from the column was methyl [3R-(3α,6α,9aβ)]-6-phthalimidooctahydro-5-oxothiazolo[3,2-a]azepine-3-carboxylate (9a(R) isomer), configuration determined by X-ray analysis), 177 mg. Recrystallization from ethyl acetate/hexane produced fine needles, m.p. 157°–157.5°; $[\alpha]_D^{25} = -32.2$ (CHCl₃); 300 MHz ¹H NMR (CDCl₃) δ1.75–2.26 (m, 5H), 2.85 (q, J=12 Hz, 1H), 3.22 (½ABq, $J_{AB}=12$ Hz, $\Delta V_{AB}=21.7$; $J_{AX}=6.5$ Hz, 1H), 3.29 (½ABq, $J_{AB}=12$ Hz, $\Delta V_{AB}=21.7$; $J_{BX}=2$ Hz, 1H), 3.79 (s, 3H), 4.99 (d, J=12 Hz, 1H), 5.15 (d, J =10 Hz, 1H), 5.34 (dd, $J_{AX}=6.5$ Hz, $J_{BX}=2$ Hz, 1H), 7.74 (m,2H), 7.87 (m,2H); I.R. (KBr): 1750, 1710, and 1640 cm⁻¹.

Anal. Calcd. for $C_{18}H_{18}N_2O_5S$: C, 57.74; H, 4.84; N, 7.48; S, 8.57. Found: C, 58.04; H, 4.90; N, 7.43; S, 8.62.

EXAMPLE 6

Ethyl [3R-(3α,6α,9aα)]-6-phthalimidooctahydro-5-oxo-thiazolo-[3,2-a]azepine-3-carboxylate and ethyl [3R-(3α,6α,9aβ)]-6-phthalimidooctahydro-5-oxo-thiazolo[3,2-a]-azepine-3-carboxylate A solution of L-cysteine ethyl ester (0.205 g) and 5-formyl-2(S)-phthalimidopentanoic acid (0.379 g) in 10 ml of dry tetrahydrofuran was stirred for 2 hours under nitrogen. Concentration of the reaction mixture yielded a foam. This residue was dissolved in 150 ml of chloroform and washed with water (2×25 ml). The aqueous layers were back-washed with chloroform (2×25 ml). The organic layers were dried and then concentrated under reduced pressure to give a white foam, 0.554 g. Tlc on silica [4:1 ethyl acetate:acetic acid] indicated a major spot at $R_f=0.80$. This thiazolidine was dissolved in dry tetrahydrofuran (15 ml) and treated with N-ethoxycarbonyl-2-ethoxy-1,2-dihydroquinoline (EEDQ). The reaction mixture was stirred for four days under nitrogen. Concentration afforded an oil which was dissolved in 150 ml of ethyl acetate and washed with 0.5 N hydrochloric acid, 5% sodium bicarbonate solution, water, and brine. After drying with Na₂SO₄, the product (0.681 g) was chromatographed on silica gel (3:2 Hexane:ethyl acetate, $R_f=0.26$) to afford a mixture of diastereomers, wt. 0.294 g. HPLC analysis (reverse phase) indicated a 50:50 mixture of isomers. The mass spectrum showed a molecular ion at 388 m/e. ¹H NMR (200 MHz, CDCl₃) δ1.28 (t, J=7 Hz) 1.32 (t, J=7 Hz) [3H], 1.68–2.40 (m, 5H), 2.82 (m, 1H), 3.20 (m, 2H), 4.19 (m, 2H), 4.94 (d, J=12 Hz) 5.06–5.30 (m) [3H], 7.66 (m, 2H), 7.79 (m, 2H).

Diastereomers can be separated by chromatography.

EXAMPLE 7

Methyl [3R-(3α,6α,9aβ)]-6-aminooctahydro-5-oxo-thiazolo[3,2-a]azepine-3-carboxylate hydrochloride Methyl [3R-(3α,6α,9aβ)]-6-phthalimidooctahydro-5-oxothiazolo[3,2-a]azepine-3-carboxylate (259 mg) was dissolved in 15 ml of absolute ethanol with gentle heating. Hydrazine hydrate (0.037 ml) was added and the mixture stirred at room temperature for 4 days under nitrogen. After concentration under vacuum to dryness, the residue was treated with 20 ml of 0.5 M HCl at 0° for 3 hours. The precipitated phthalhydrazide was filtered off and the filtrate freeze-dried to yield 220 mg of product. Tlc on silica (1:1:1:1 ethyl acetate:n-butanol:-water:acetic acid) indicated a single spot by ninhydrin, $R_f=0.63$. ¹H NMR (200 MHz, CD₃OD) δ1.8–2.18 (m, 6H), 3.30 (2H), 3.77 (s, 3H), 4.26 (d, J=9 Hz, 1H), 5.17 (dd, J=7 Hz, J=3.5 Hz, 1H), 5.25 (t, J=4.5 Hz, 1H); exact mass measurement (free base), Obs. 244.0878, calcd. 244.0881.

EXAMPLE 8

[3R-(3α,6α,9aβ)]-6-Aminooctahydro-5-oxo-thiazolo[3,2-a]azepine-3-carboxylic acid Methyl [3R-(3α,6α,9aβ)]-6-aminooctahydro-5-oxo-thiazolo[3,2-a]azepine-3-carboxylate (220 mg) was dissolved in 5 ml of CH₃OH and treated with 4.3 ml of 1 M NaOH at room temperature overnight. The reaction mixture was absorbed on 15 ml of strong acid ion-exchange resin and eluted with 3% pyridine in water to yield 133 mg of product. Tlc on silica [1:1:1:1 ethyl acetate:n-butanol:water:acetic acid] indicated a single spot at $R_f=0.56$. Recrystallized from methanol, m.p. 208°–210° (dec); $[\alpha]_D^{25} = -84.5°$ (c=1.58, 1 N HCl); ¹H NMR (200 MHz, D₂O) δ2.02 (m, 6H), 3.27 (d, J=5 Hz, 2H), 4.32 (m, 1H), 4.97 (t, J=5 Hz, 1H), 5.16 (m, 1H).

Anal. Calcd. for $C_9H_{14}N_2O_3S$: C, 46.94; H, 6.13; N, 12.17; S, 13.93. Found: C, 46.66; H, 6.34; N, 12.01; S, 13.69.

EXAMPLE 9

Methyl [3R-[3α,6α(S*R*),9aβ]]-6-[(1-methoxycarbonyl-3-phenylpropyl)amino]octahydro-5-oxothiazolo-[3,2-a]azepine-3-carboxylate A solution of methyl [3R-[3α,6α,9aβ]]-6-aminooctahydro-5-oxothiazolo[3,2-a]azepine-3-carboxylate hydrochloride (414 mg) in aqueous methanol was adjusted to pH=6.25 with 1 M NaOH. The mixture was concentrated and then redissolved in absolute methanol (20 ml). Methyl 2-oxo-4-phenylbutyrate (1.42 g) and 3 A powdered molecular sieves (4 g) were added. A solution of sodium cyanoborohydride (277 mg) in 4 ml of methanol was added via a syringe pump over 24 hours. When reaction was complete, the sieves were removed by filtration and the filtrate concentrated. The residue was partitioned between $CH_2Cl_2$ and water. The $CH_2Cl_2$ layer was dried and concentrated to dryness. The mixture of diastereomers was separated by silica gel chromatography with 1:1 hexane:ethyl acetate as eluant.

The first diastereomer ($R_f$=0.23) eluted from the column was methyl [3R-[3α,6α(R*),9aβ]]-6-[(1-methoxycarbonyl-3-phenylpropyl)amino]octahydro-5-oxothiazolo[3,2-a]azepine-3-carboxylate, 177 mg; 'H NMR (200 MHz, $CDCl_3$) δ1.52–2.14 (m, 8H), 2.71 (t, J=8 Hz, 2H), 3.18 (m, 4H), 3.66 (s, 3H), 3.73 (s, 3H), 4.85 (d, J=9 Hz, 1H), 5.27 (dd, J=7 Hz, J=3 Hz, 1H), 7.26 (m, 5H); exact mass measurement, obs. 420.1711, calcd. 420.1718; $[α]_D^{25°}$= −42.9° ($CHCl_3$).

Anal. Calcd. for $C_{21}H_{28}N_2O_5S$: C, 59.98; H, 6.71; N, 6.66; S, 7.63. Found: C, 59.98; H, 6.76; N, 6.49; S, 7.35.

The second diastereomer ($R_f$=0.29) eluted from the column was methyl [3R-[3α,6α(S*),9aβ]]-6-[(1-methoxycarbonyl-3-phenylpropyl)amino]octahydro-5-oxothiazolo[3,2-a]azepine-3-carboxylate, 290 mg; 'H NMR (200 MHz, $CDCl_3$) δ1.62–2.24 (m, 8H), 2.74 (t, J=8 Hz, 2H), 3.14–3.46 (m, 4H), 3.73 (s, 3H), 3.80 (s, 3H), 4.99 (d, J=9 Hz, 1H), 5.28 (dd, J=7 Hz, J=3 Hz, 1H), 7.28 (m, 5H); exact mass measurement, obs. 420.1711, calcd. 420.1718; I.R. 1730 and 1650 cm$^{-1}$; $[α]_D^{25°}$= −65.8° ($CHCl_3$).

Anal. Calcd. for $C_{21}H_{28}N_2O_5S$: C, 59.98; H, 6.71; N, 6.66; S, 7.63. Found: C, 60.24; H, 6.80; N, 6.47; S, 7.57.

EXAMPLE 10

[3R-[3α,6α(S*),9aβ]]-6-[(1-Carboxy-3-phenylpropyl)amino]octahydro-5-oxothiazolo[3,2-a]azepine-3-carboxylic acid Methyl [3R-[3α,6α(S*),9aβ]]-6-[(1-methoxycarbonyl-3-phenylpropyl)amino]octahydro-5-oxothiazolo-[3,2-a]azepine-3-carboxylate (180 mg) was dissolved in 2 ml of $CH_3OH$ and 2 ml of 1 M NaOH. After standing overnight, the product was absorbed on strong acid ion-exchange resin and eluted with 3% pyridine in water. Appropriate fraction was concentrated and dried in vacuo to afford a white solid, 165 mg. Recrystallized from methanol, m.p. 212°–13° (dec); $[α]_D^{25°}$= −90.9° (0.1 N NaOH, c=0.2); I.R. (KBr) 1718 and 1654 cm$^{-1}$; Tlc on silica [1:1:1:1 ethyl acetate:n-butanol:water:acetic acid] indicated a single product, $R_f$=0.78; 'H NMR (200 MHz, $d_6$-DMSO) δ1.36–2.20 (m, 8H), 2.69 (m, 2H), 3.24 (m, 3H), 3.81 (d, J=10 Hz, 1H), 5.07 (dd, J=7 Hz, J=3.5 Hz, 1H) 5.19 (d, J=8 Hz, 1H), 7.26 (m, 5H). The mass spectrum showed a molecular ion at 536 m/e for the disilylated species. X-ray crystal structure analysis established the stereochemistry of the side chain as (S).

Anal. Calcd. for $C_{19}H_{24}N_2O_5S \cdot \frac{1}{2}H_2O$: C, 56.84; H, 6.28; N, 6.98; S, 7.99. Found: C, 56.68; H, 6.11; N, 6.82; S, 7.87.

EXAMPLE 11

[3R-[3α,6α(R*),9aβ]]-6-[(1-Carboxy-3-phenylpropyl)amino]octahydro-5-oxothiazolo[3,2-a]azepine-3-carboxylic acid Methyl [3R-[3α,6α(R*),9aβ]]-6-[(1-methoxycarbonyl-3-phenylpropyl)amino]octahydro-5-oxothiazolo[3,2-a]azepine-3-carboxylate (100 mg) was dissolved in 1 ml of methanol and treated with 1 ml of 1 M NaOH. After standing overnight, the product was absorbed on strong acid ion-exchange resin and eluted with 3% pyridine in $H_2O$. Concentration and drying afforded a white solid, 93 mg. Recrystallized from methanol, m.p. 250°–51° (dec). Tlc on silica [1:1:1:1 ethyl acetate:n-butanol:water:acetic acid] indicated a single spot, $R_f$=0.73. $[α]_D^{25°}$= −67.7° (0.1 N NaOH, c=0.2). 'H NMR (200 MHz, $CD_3OD$) δ1.68–2.36 (m, 8H), 2.75 (m, 2H), 3.24 (m, 2H), 3.68 (t, J=5 Hz, 1H), 4.04 (d, J=10 Hz, 1H), 5.04 (d, J=9 Hz, 1H), 5.16 (dd, J=5 Hz, J=3 Hz, 1H), 7.24 (m, 5H). The mass spectrum showed a molecular ion at 536 m/e for the disilylated species.

Anal. Calcd. for $C_{19}H_{24}N_2O_5S$: C, 58.14; H, 6.16; N, 7.14; S, 8.17. Found: C, 57.95; H, 6.22; N, 6.98; S, 8.12.

EXAMPLE 12

[3R-[3α,6α(S*R*),9aβ]]-6-[(1-Carboxy-3-phenylpropyl)amino]octahydro-5-oxothiazolo[3,2-a]azepine-3-carboxylic acid

[3R-(3α,6α,9aβ)]-6-Aminooctahydro-5-oxothiazolo[3,2-a]azepine-3-carboxylic acid (83 mg) and 2-oxo-4-phenylbutyric acid (0.32 g) were suspended in 5 ml of $H_2O$ and adjusted to pH 6.0 with 1 M NaOH. Sodium cyanoborohydride (45 mg) in 2 ml of $H_2O$ was slowly added. When reaction was complete, the reaction mixture was absorbed on strong acid ion-exchange resin and eluted with 3% pyridine in $H_2O$ to yield product, wt. 117 mg. Tlc on silica [1:1:1:1 ethyl acetate:n-butanol:water:acetic acid] indicated two spots, $R_f$=0.73 and 0.78. The mass spectrum showed a molecular ion at 536 m/e for the disilylated species. 'H NMR (60 MHz, $CD_3OD$) δ 1.5–2.45 (m, 8H), 2.75 (m, 2H), 3.25 (m, 2H), 3.60 (m, 1H), 4.10 (m, 1H), 5.01 (m, 2H), 7.18 (s, 5H).

EXAMPLE 13

[3R-[3α,6α(S*),9aβ]]-6-[(1-Ethoxycarbonyl-3-phenylpropyl)amino]octahydro-5-oxothiazolo[3,2-a]azepine-3-carboxylic acid and
[3R-[3α,6α(R*),9aβ]]-6-[(1-ethoxycarbonyl-3-phenylpropyl)amino]octahydro-5-oxothiazolo[3,2-a]azepine-3-carboxylic acid A solution of [3R-(3α,6α,9aβ)]-6-aminooctahydro-5-oxothiazolo[3,2-a]azepine-3-carboxylic acid (345 mg) in 10 ml of $H_2O$ was adjusted to pH 6.3 with dilute NaOH. The solution was then freeze-dried. The residue and ethyl 2-oxo-4-phenylbutyrate (1.55 g) were partly dissolved in 25 ml of absolute ethanol. Powdered 3 A molecular sieves (3.5 g) were added. To this mixture, a solution of sodium cyanoborohydride (282 mg) in 5 ml of ethanol was slowly added via a syringe pump. After completion of the reaction, the mixture was filtered and the filtrate taken to dryness. The residue was partitioned between water (100 ml) and ether (50 ml). The layers were separated. The aqueous layer was absorbed on strong acid ion-exchange resin and eluted with water, then 3% pyridine in water to yield the title product as a mixture of diastereomers, wt. 638 mg. Tlc on silica [1:1:1:1 ethyl acetate:n-butanol:water:acetic acid] indicated a major spot at $R_f$=0.80. Diastereomers were separated by chromatography on Sephadex LH-20 (MeOH, 2.54 cm×2 m).

The first diastereomer to elute from the column was [3R-[3α,6α(S*),9aβ]]-6-[(1-ethoxycarbonyl-3-phenylpropyl)amino]octahydro-5-oxothiazolo [3,2-a]azepine-3-carboxylic acid, wt. 338 mg; exact mass measurement, obs. 420.1715, calcd. 420.1718; $^1$H NMR (200 MHz, CDCl$_3$) δ1.29 (t, J=6 Hz, 3H), 1.56–2.22 (m, 8H), 2.74 (t, J=8 Hz, 2H), 3.18 (m, 1H), 3.42 (m, 3H), 3.77 (br s, 2H, exchangeable), 4.20 (m, 2H), 4.96 (d, J=8 Hz, 1H), 5.19 (br s, 1H), 7.25 (m, 5H). $^{13}$C NMR spectrum in CDCl$_3$/MeOH (3:1) showed single absorptions at 174.5, 172.8, 141.4, 128.7, 126.3, 64.1, 62.9, 61.4, 60.4, 60.3, 35.7, 34.9, 32.2, 31.9, 31.5, 28.3, and 14.4 ppm.

The second diastereomer to elute from the column was [3R-[3α,6α(R*),9aβ]]-6-[(1-ethoxycarbonyl-3-phenylpropyl)amino]octahydro-5-oxothiazolo[3,2-a]azepine -3-carboxylic acid, wt. 101 mg; exact mass measurement, obs. 420.1727, calcd. 420.1718; $^1$H NMR (200 MHz, CDCl$_3$) δ1.28 (t,J=7 Hz, 3H), 1.54–2.22 (m, 8H), 2.77 (t, J=7 Hz, 2H), 3.15 (m, 1H), 3.34 (m, 3H), 3.54 (br s, 2H, exchangeable), 4.19 (q, J=7 Hz, 2H), 4.88 (d, J=7 Hz, 1H), 5.24 (d, J=5 Hz, 1H), 7.27 (m, 5H).

EXAMPLE 14

[3R-[3α,6α(S*),9aβ]]-6-[(1-Ethoxycarbonyl-3-phenylpropyl)amino]octahydro-5-oxothiazolo[3,2-a]azepine-3-carboxylic acid hydrochloride Anhydrous hydrogen chloride was bubbled into a solution of [3R-[3α,6α(S*),9aβ]]-6-[(1-ethoxycarbonyl-3-phenylpropyl)amino]octahydro-5-oxothiazolo[3,2-a]azepine-3-carboxylic acid (320 mg) in ethyl acetate (30 ml) at 0°. Precipitate was collected, wt. 305 mg; m.p. 224°–25° (dec); $[α]_D^{25°}$ = −38.5° (EtOH, c=1.2); I.R. (KBr): 1730, 1690, and 1658 cm$^{-1}$; Tlc on silica [1:1:1:1 ethyl acetate:n-butanol:water:acetic acid] indicated a single spot at $R_f$=0.81.

Anal. Calcd. for C$_{21}$H$_{28}$N$_2$O$_5$S-HCl-½H$_2$O: C, 54.12; H, 6.49; N, 6.01; S, 6.88; Cl, 7.61. Found: C, 54.19; H, 6.47; N, 6.07; S, 6.71, Cl, 7.85.

EXAMPLE 15

[3R-[3α,6α(R*),9aβ]]-6-[(1-Ethoxycarbonyl-3-phenylpropyl)amino]octahydro-5-oxothiazolo[3,2-a]azepine-3-carboxylic acid hydrochloride Anhydrous hydrogen chloride was bubbled into a solution of [3R-[3α,6α(R*),9aβ]]-6-[(1-ethoxycarbonyl-3-phenylpropyl)amino]octahydro-5-oxothiazolo[3,2-a]azepine-3-carboxylic acid (120 mg) in ethyl acetate (20 ml) at 0°. Precipitate was collected, wt. 122 mg; m.p. 123°–25°; $[α]_D^{25°}$= −77.2° (EtOH, c=0.6); Tlc on silica [1:1:1:1 ethyl acetate:n-butanol:water:acetic acid] indicated a single spot at $R_f$=0.85.

Anal. Calcd. for C$_{21}$H$_{28}$N$_2$O$_5$S-HCl-0.25 H$_2$O: C, 54.65; H, 6.44; N, 6.07; S, 6.95; Cl, 7.68. Found: C, 54.75; H, 6.40; N, 5.90; S, 6.83; Cl, 7.29.

EXAMPLE 16

[3R-[3α,6α(S*),9aβ]]-6-[(1-Carboxy-3-phenylpropyl)amino]octahydro-5-oxothiazolo[3,2-a]azepine-3-carboxylic acid A solution of [3R-[3α,6α(S*),9aβ]]-6-[(1-ethoxycarbonyl-3-phenylpropyl)amino]octahydro-5-oxothiazolo[3,2-a]azepine-3-carboxylic acid hydrochloride (147 mg) in 2.5 ml of methanol was treated with 1.6 ml of 1 M NaOH solution. After standing overnight, the reaction mixture was absorbed on strong acid ion-exchange resin. Elution with water and then 4% pyridine in water permitted recovery of product, wt. 126 m. This material was identical to that described in Example 10.

EXAMPLE 17

Ethyl [3R-[3α,6α(S*),9aβ]]-6-[(1-Ethoxycarbonyl-3-phenylpropyl)amino]octahydro-5-oxothiazolo[3,2-a]azepine-3-carboxylate hydrochloride Anhydrous hydrogen chloride was bubbled through a solution of [3R-[3α,6α(S*),9aβ]]-6-[(1-ethoxycarbonyl-3-phenylpropyl)amino]octahydro-5-oxothiazolo[3,2-a]azepine-3-carboxylic acid hydrochloride (116 mg) in absolute ethanol (30 ml) at 0° for 10 minutes. The reaction mixture was stirred overnight at room temperature and then taken to dryness under reduced pressure. The residue was partitioned between H$_2$O (10 ml) and ether (20 ml). To this mixture, 0.28 ml of 1 M NaOH solution was added. After a few minutes, the layers were separated. The ethereal layer was dried (Na$_2$SO$_4$) and then concentrated to give 100 mg of product. Chromatography on silica gel (2:1 Hexane:ethyl acetate, $R_f$=0.26) afforded 80 mg of pure product. The mass spectrum showed a molecular ion at 448. $^1$H NMR (300 MHz, CDCl$_3$) δ1.32 (2 triplets, 6H), 1.60 (br s, 1H), 1.68–2.20 (m, 8H), 2.75 (t, J=8 Hz, 2H), 3.28 (m, 2H), 3.4 (m, 2H), 4.25 (m, 4H), 5.01 (d, J=10 Hz, 1H), 5.29 (dd, J=6 Hz, J=3 Hz, 1H), 7.28 (m, 5H). Anhydrous hydrogen chloride was bubbled through a solution of the purified diester in ether (30 ml) at 0°. Excess HCl was removed and the title product was collected by filtration, wt. 84 mg; m.p. 68°–70°; $[α]_D^{25°}$= −52.98° (EtOH, c=0.44).

Anal. Calcd. for C$_{23}$H$_{32}$N$_2$O$_5$S-HCl-¼H$_2$O: C, 56.43; H, 6.90; N, 5.72. Found: C, 56.47; H, 6.95; N, 5.42.

EXAMPLE 18

Benzyl [3R-(3α,6α,9aβ)]-6-Aminooctahydro-5-oxothiazolo[3,2-a]azepine-3-carboxylate

[3R-(3α,6α,9aβ)]-6-Aminooctahydro-5-oxothiazolo[3,2-a]azepine-3-carboxylic acid (205 mg) was suspended in 2.5 ml of benzyl alcohol and cooled with an ice bath. Thionyl chloride (0.26 ml) was added. After a few minutes, ice bath was removed and the mixture stirred at room temperature under nitrogen overnight. Ether (30 ml) was added and the resulting precipitate collected, wt. 313 mg. This material was suspended in 20 ml of H$_2$O and treated with 0.878 ml of 1 M NaOH solution. After a few minutes, the mixture was extracted with CH$_2$Cl$_2$ (3×20 ml). The organic layers were dried (Na$_2$SO$_4$) and concentrated to give 193 mg of pure product. Tlc on silica [1:1:1:1 ethyl acetate:n-butanol:water:acetic acid] indicated a single spot at $R_f$=0.74. Mass spectrum showed a molecular ion at 320 m/e. $^1$H NMR (200 MHz, CDCl$_3$) δ 1.40–2.02 (m, 6H), 1.68 (br s, —NH$_2$), 3.15 (m, 2H), 3.47 (d, J=11 Hz, 1H), 4.92 (d, J=8 Hz, 1H), 5.15 (s, 2H), 5.28 (dd, J=7 Hz, J=3 Hz, 1H), 7.32 (s, 5H).

EXAMPLE 19

Benzyl [3R-[3α,6α(S*R*),9aβ]]-6-[(1-tert.butoxycarbonyl-3-phenylpropyl)amino]octahydro-5-oxothiazolo[3,2-a]azepine-3-carboxylate To a solution of Benzyl [3R-(3α,6α,9aβ)]-6-aminooctahydro-5-oxothiazolo[3,2-a]azepine-3-carboxylate (249 mg) and t-butyl 2-oxo-4-phenylbutyrate (910 mg) in absolute ethanol (12 ml), powdered 3 A molecular sieves (2.5 g) and 0.045 ml of acetic acid were added. To this mixture, a solution of sodium cyanoborohydride (146 mg) in 2.5 ml of ethanol was added slowly (syringe pump). When reaction was completed, the mixture was filtered and the filtrate concentrated. The residue was partitioned between water and CH$_2$Cl$_2$. The organic layer was dried (Na$_2$SO$_4$) and concentrated to afford an oil, wt. 1.1 g. Chromatography on silica [3:1 hexane:ethyl acetate] permitted the isolation of the diastereomers: R* diastereomer, 101 mg; exact mass measurement, obs. 538.2470; calcd., 538.2500; 'H NMR (200 MHz, CDCl$_3$) 1.47 (s, 9H), 1.52–2.14 (m, 8H), 2.76 (t, J=8 Hz, 2H), 3.20 (m, 4H), 4.86 (d, J=9 Hz, 1H), 5.21 (q, 2H), 5.40 (dd, J=6 Hz, J=3 Hz, 1H), 7.26 (m, 5H), 7.39 (s, 5H). S* diastereomer, 120 mg; exact mass measurement, obs. 538.2465; calcd. 538.2500; 'H NMR (200 MHz, CDCl$_3$) δ1.50 (s, 9H), 1.55–2.16 (m, 8H), 2.32 (br s, N—H), 2.73 (t, J=8 Hz, 2H), 3.25 (m, 4H), 4.97 (d, J=10 Hz, 1H), 5.22 (q, 2H), 5.34 (dd, J=7 Hz, J=2.5 Hz, 1H), 7.26 (m, 5H), 7.39 (m, 5H).

EXAMPLE 20

Benzyl [3R-[3α,6α(S*),9aβ]]-6-[(1-carboxy-3-phenylpropyl)amino]octahydro-5-oxothiazolo[3,2-a]azepine-3-carboxylate hydrochloride A solution of Benzyl [3R-[3α,6α(S*),9aβ]]-6-[(1-tert.butoxycarbonyl-3-phenylpropyl)amino]octahydro-5-oxothiazolo[3,2-a]azepine-3-carboxylate (118 mg) in 4 N HCl/ethyl acetate was prepared at 0°. The solution was then stirred at room temperature for 3 hours. Concentration and tituration with ether gave the title compound, wt. 114 mg. The mass spectrum showed a molecular ion at 482 m/e for the free base. Tlc on silica [4:1:1:1 ethyl acetate:n-butanol:water:acetic acid] indicated a single spot, R$_f$=0.57. [α]$_D^{25°}$= −49.9° (EtOH, c=0.48); m.p. 111°–113°; 'H NMR (200 MHz, CD$_3$OD) 1.72–2.48 (m, 8H), 2.89 (m, 2H), 3.35 (m, 2H), 4.05 (t, J=6 Hz, 1H), 4.35 (d, J=10.5 Hz, 1H), 5.19 (m, 1H), 5.27 (q, 2H), 5.35 (t, J=4.5 Hz, 1H), 7.38 (m, 10H).

Anal. Calcd. for C$_{26}$H$_{30}$N$_2$O$_5$S·HCl: C, 60.16; H, 6.02; N, 5.40. Found: C, 59.81; H, 6.12; N, 5.15.

EXAMPLE 21

Ethyl [3R-[3α,6α,9aβ]]-6-Aminooctahydro-5-oxothiazolo[3,2-a]azepine-3-carboxylate

[3R-(3α,6α,9aβ)]-6-Aminooctahydro-5-oxothiazolo[3,2-a]azepine-3-carboxylic acid was dissolved in absolute ethanol which was saturated with anhydrous hydrogen chloride at 0°. The reaction mixture was permitted to stand at room temperature overnight. The mixture was then taken to dryness and the residue neutralized in water. Extraction with CH$_2$Cl$_2$ permitted the recovery of the desired product which exhibited spectral properties consistent with its structure.

EXAMPLE 22

Ethyl [3R-[3α,6α(S*R*),9aβ]]-6-[(1-carboxy-3-phenylpropyl)amino]octahydro-5-oxothiazolo[3,2-a]azepine-3-carboxylate hydrochloride To a solution of ethyl [3R-[3α,6α,9aβ]]-6-aminooctahydro-5-oxothiazolo[3,2-a]azepine-3-carboxylate and t-butyl 2-oxo-4-phenylbutyrate in absolute ethanol, powdered 3 A molecular sieves and one equivalent of acetic acid were added. To this mixture, a solution of sodium cyanoborohydride in ethanol was slowly added via a syringe pump. When the reaction was completed, the sieves were removed by filtration and the filtrate concentrated. The residue was partitioned between water and CH$_2$Cl$_2$. Concentration of the organic phase afforded a mixture of α-ketoester, α-hydroxyester, and the product, ethyl [3R-[3α,6α(S*R*),9aβ]]-6-[(1-tert.butoxycarbonyl-3-phenylpropyl)amino]octahydro-5-oxothiazolo[3,2-a]azepine-3-carboxylate. Chromatography on silica permitted the isolation of each diastereomer in high purity. Each diastereomer was deblocked with 4 N HCl in ethyl acetate to give the title compounds which exhibited the expected spectral characteristics.

EXAMPLE 23

[3R-[3α,6α(S*R*),9aβ]]-6-[(1-Benzyloxycarbonyl-3-phenylpropyl)amino]octahydro-5-oxothiazolo[3,2-a]azepine-3-carboxylic acid A solution of [3R-(3α,6α,9aβ)]-6-aminooctahydro-5-oxothiazolo[3,2-a]azepine-3-carboxylic acid (200 mg) in 10 ml of H$_2$O was adjusted to pH 6.3 with 0.5 M NaOH solution. The solution was freeze-dried. This residue and benzyl 2-oxo-4-phenylbutyrate (1.165 g) were partly dissolved in absolute ethanol (10 ml). Powdered 3 A molecular sieves (2.25 g) were added. To this mixture, a solution of sodium cyanoborohydride (164 mg) in 2 ml of ethanol was slowly added via a syringe pump. When the reaction was completed, the mixture was filtered and the filtrate concentrated. The residue was partitioned between ether (25 ml) and water (25 ml). After separation of the layers, the aqueous phase was adjusted to pH 4.5 with 1 M H$_3$PO$_4$. This acidified mixture was then repeatedly extracted with chloroform. The organic portion was dried and concentrated to give 239 mg of product. The diastereomers were separated by chromatography on Sephadex LH-20 (MeOH).

The first diastereomer to elute from the column was the (S*) isomer; wt. 0.103 g. The mass spectrum showed a weak molecular ion at 482 m/e. Tlc on silica [1:1:1:1 Ethyl acetate:n-butanol:water:acetic acid] indicated a single spot, R$_f$=0.85. 'H NMR (200 MHz, CD$_3$OD) δ1.52–2.24 (m, 8H), 2.65 (m, 2H), 3.06–3.37 (m, 2H), 3.69 (m, 2H), 4.92 (m, 1H), 5.09 (m, 1H), 5.26 (q, 2H), 7.22 (m, 5H), 7.45 (m, 5H).

The second diastereomer to elute from the column was the (R*) isomer, wt. 66 mg. The mass spectrum showed a (M-1) ion at 481. Tlc on silica [1:1:1:1 ethyl acetate:n-butanol:water:acetic acid] indicated a single spot, R$_f$=0.86. 'H NMR (200 MHz, CD$_3$OD) δ1.50–2.14 (m, 8H), 2.66 (m, 2H), 3.03–3.30 (m, 3H), 3.43 (t, J=7 Hz, 1H), 4.78 (d, J=9 Hz, 1H), 5.09 (m, 1H), 5.20 (q, 2H), 7.22 (m, 5H), 7.42 (m, 5H).

EXAMPLE 24

[3R-[3α,6α(S*),9aβ]]-6-[(1-Benzyloxycarbonyl-3-phenylpropyl)amino]octahydro-5-oxothiazolo[3,2-a]azepine-3-carboxylic acid hydrochloride Anhydrous hydrogen chloride was bubbled through a solution of [3R-[3α,6α(S*),9aβ]]-6-[(1-benzyloxycarbonyl-3-phenylpropyl)amino]octahydro-5-oxothiazolo[3,2-a]azepine-3-carboxylic acid (85 mg) in ethyl acetate (10 ml). Upon removal of excess HCl, the precipitate was collected, wt. 93.7 mg $[\alpha]_D^{25°} = -44.1°$ (EtOH, c=0.3).

Anal. Calcd. for $C_{26}H_{30}N_2O_5S \cdot HCl$: C, 60.16; H, 6.02; N, 5.40; S, 6.18; Cl, 6.83. Found: C, 59.78; H, 6.06; N, 5.25; S, 6.19; Cl, 6.36.

EXAMPLE 25

[3R-[3α,6α(S*R*),9aβ]]-6-[(1-Methoxycarbonyl-3-phenylpropyl)amino]octahydro-5-oxothiazolo[3,2-a]azepine-3-carboxylic acid To a solution of [3R-(3α,6α,9aβ)]-6-aminooctahydro-5-oxothiazolo[3,2-a]azepine-3-carboxylic acid (252 mg) and methyl 2-oxo-4-phenylbutyrate (1.05 g) in methanol (20 ml), powdered 3 A molecular sieves (2.8 g) were added. To this mixture, a solution of sodium cyanoborohydride (205 mg) in 2 ml of methanol was slowly added via a syringe pump. When the reaction was completed, the mixture was filtered and the filtrate taken to dryness. The residue was partitioned between ether (30 ml) and water (30 ml). The layers were separated and the aqueous layer acidified with 1 M $H_3PO_4$ to pH 3.5. The acidified layer was then extracted repeatedly with chloroform. The chloroform extracts are dried and concentrated to yield 370 mg of the diastereomeric mixture. Separation of diastereomers was achieved by chromatography on Sephadex LH-20 (MeOH).

The first diastereomer to elute from the column was the (S*) isomer; wt. 0.180 g. The mass spectrum showed a molecular ion at 478 m/e for the monosilylated species. $^1$H NMR (200 MHz, CD$_3$OD) δ 1.74–2.28 (m, 8H), 2.77 (t, J=7 Hz, 2H), 3.26 (m, 2H), 3.70 (t, J=6 Hz, 1H), 3.77 (s, 3H), 3.84 (m, 1H), 5.13 (m, 2H), 7.28 (m, 5H).

The second diastereomer was the (R*) isomer; wt. 0.101 g. The mass spectrum showed a molecular ion at 406 m/e. $^1$H NMR (200 MHz, CD$_3$OD) δ1.64–2.20 (m, 8H), 2.74 (t, J=7 Hz, 2H), 3.27 (m, 2H), 3.46 (m, 2H), 3.74 (s, 3H), 5.06 (d, J=11 Hz, 1H), 5.13 (dd, J=7 Hz, J=3 Hz, 1H), 7.26 (m, 5H).

EXAMPLE 26

[3R-[3α,6α(S*),9aβ]]-6-[(1-Methoxycarbonyl-3-phenylpropyl)amino]octahydro-5-oxothiazolo[3,2-a]azepine-3-carboxylic acid hydrochloride Anhydrous hydrogen chloride was bubbled through a solution of [3R-[3α,6α(S*),9aβ]]-6-[(1-methoxycarbonyl-3-phenylpropyl)amino]octahydro-5-oxothiazolo[3,2-a]azepine-3-carboxylic acid (0.180 g) in ethyl acetate (20 ml) at 0°. Upon removal of excess HCl, the precipitate was collected, wt. 0.188 g $[\alpha]_D^{25°} = -39.5°$ (MeOH, c=1.6).

Anal. Calcd. for $C_{20}H_{26}N_2O_5S \cdot HCl$: C, 54.23; H, 6.14; N, 6.32; S, 7.24; Cl, 8.00. Found: C, 54.14; H, 6.10; N, 6.01; S, 7.17; Cl, 7.93.

EXAMPLE 27

[3R-[3α,6α(R*),9aβ]]-6-[(1-Methoxycarbonyl-3-phenylpropyl)amino]octahydro-5-oxothiazolo[3,2-a]azepine-3-carboxylic acid hydrochloride Anhydrous hydrogen chloride was bubbled through a solution of [3R-[3α,6α(R*),9aβ]]-6-[(1-methoxycarbonyl-3-phenylpropyl)amino]octahydro-5-oxothiazolo[3,2-a]azepine-3-carboxylic acid (0.1 g) in ethyl acetate (10 ml) at 0°. Upon removal of excess HCl, the precipitate was collected, wt. 0.105 g $[\alpha]_D^{25°} = 74.1°$ (MeOH, c=0.7).

Anal. Calcd. for $C_{20}H_{26}N_2O_5S \cdot HCl \cdot H_2O$: C, 52.11; H, 6.34; N, 6.08; S, 6.96; Cl, 7.69. Found: C, 52.14; H, 5.98; N, 5.68; S, 6.95; Cl, 7.87.

EXAMPLE 28

[3R-[3α,6α(S*R*),9aβ]]-6-[(1-Ethoxycarbonyl-4-methylpentyl)amino]octahydro-5-oxothiazolo[3,2-a]azepine-3-carboxylic acid To a solution of [3R-(3α,6α,9aβ)]-6-aminooctahydro-5-oxothiazolo[3,2-a]azepine-3-carboxylic acid (0.348 g) and ethyl 5-methyl-2-oxo-hexanoate (1.30 g) in absolute ethanol (15 ml), powdered 3 A molecular sieves (3.9 g) were added. To this mixture, a solution of sodium cyanoborohydride (0.285 g) in ethanol (2 ml) was slowly added. When the reaction was completed, the mixture was filtered and the filtrate concentrated to dryness. The residue was partitioned between water (35 ml) and ether (35 ml) and the layers were separated. The aqueous layer was acidified with 1 M $H_3PO_4$ to pH 4.5 and then extracted repeatedly with chloroform. The chloroform layers were dried and then concentrated to yield product, wt. 0.538 g. Separation of the (S*,R*) diastereomers was achieved by chromatography on Sephadex LH-20 (MeOH).

The first diastereomer off the column was the (S*) isomer: wt. 0.219 g; exact mass measurement, obs. 386.1855, calcd. 386.1874. Tlc on silica [1:1:1;1 ethyl acetate:n-butanol:water:acetic acid] indicated a single spot, R$_f$=0.83. $^1$H NMR (200 MHz, CD$_3$OD) δ0.92 (dd, J=7 Hz, J=2.5 Hz, 6H), 1.30 (t, J=7 Hz, 3H), 1.32 (m, 2H), 1.57 (m, 1H), 1.70–2.26 (m, 8H), 3.24 (m, 2H), 3.68 (t, J=6.5 Hz, 1H), 3.86 (d, J=10 Hz, 1H), 4.26 (m, 2H), 5.08 (m, 2H).

The second diastereomer to elute from the column was the (R*) isomer: wt. 0.210 g; exact mass measurement, obs. 386.1847, calcd. 386.1874. $^1$H NMR (200 MHz, CD$_3$OD) δ0.91 (d, J=7 Hz, 6H), 1.20 (m, 2H), 1.28 (t, J=8 Hz, 3H) 1.54 (m, 1H), 1.64–2.20 (m, 8H), 3.23 (m, 2H), 3.49 (m, 2H), 4.21 (m, 2H), 5.13 (m, 2H).

EXAMPLE 29

[3R-[3α,6α(S*),9aβ]]-6-[(1-Ethoxycarbonyl-4-methylpentyl)amino]octahydro-5-oxothiazolo[3,2-a]azepine-3-carboxylic acid hydrochloride Anhydrous hydrogen chloride was bubbled through a solution of [3R-[3α,6α(S*),9aβ]]-6-[(1-ethoxycarbonyl-4-methylpentyl)amino]octahydro-5-oxothiazolo[3,2-a]azepine-3-carboxylic acid (114 mg) in ethyl acetate (10 ml) at 0°. Upon removal of excess HCl, the precipitate was collected, wt. 0.120 g $[\alpha]_D^{25°} = -54.7°$ (MeOH, c=0.5).

Anal. Calcd. for $C_{18}H_{30}N_2O_5S \cdot HCl \cdot 0.5H_2O$: C, 50.05; H, 7.47; N, 6.49; S, 7.42; Cl, 8.21. Found: C, 49.74; H, 7.36; N, 6.31; S, 7.39; Cl, 8.39.

EXAMPLE 30

[3R-[3α,6α(S*),9aβ]]-6-[(1-Carboxy-4-methylpentyl)amino]octahydro-5-oxothiazolo[3,2-a]azepine-3-carboxylic acid

[3R-[3α,6α(S*),9aβ]]-6-[(1-Ethoxycarbonyl-4-methylpentyl)amino]octahydro-5-oxothiazolo[3,2-a]azepine-3-carboxylic acid (105 mg) was dissolved in methanol (1.5 ml) and treated with 1.4 ml of 1 M NaOH solution. After standing overnight, the reaction mixture was absorbed on strong acid ion-exchange resin and eluted with 3% pyridine in water. The appropriate fraction was concentrated and dried in vacuo to yield a white solid, wt. 97 mg; $[\alpha]_D^{25°} = -103.9°$ (0.1 M NaOH, c=0.7). The mass spectrum showed a molecular ion at 502 m/e for the disilylated species. 'H NMR (200 MHz, CD$_3$OD) δ0.94 (dd, J=7 Hz, J=2.5 Hz, 6H), 1.41 (m, 2H), 1.59 (m, 1H), 1.76-2.36 (m, 8H), 3.30 (m, 2H), 3.60 (t, J=6 Hz, 1H), 4.20 (d, J=8 Hz, 1H), 5.20 (m, 2H).

Anal. Calcd. for $C_{16}H_{26}N_2O_5S \cdot \frac{1}{4}H_2O$: C, 52.95; H, 7.36; N, 7.72; S, 8.83. Found: C, 52.86; H, 7.44; N, 7.51; S, 8.64.

EXAMPLE 31

[3R-[3α,6α(R*),9aβ]]-6-[(1-Carboxy-4-methylpentyl)amino]octahydro-5-oxothiazolo[3,2-a]azepine-3-carboxylic acid

[3R-[3α,6α(R*),9aβ]]-6-[(1-Ethoxycarbonyl-4-methylpentyl)amino]octahydro-5-oxothiazolo[3,2-a]azepine-3-carboxylic acid (110 mg) was dissolved in methanol (1.5 ml) and treated with 1.43 ml of 1 M NaOH solution. After standing overnight, the reaction mixture was absorbed on strong acid ion-exchange resin and eluted with 3% pyridine in water. The appropriate fraction was concentrated and dried to give 96 mg of product. $[\alpha]_D^{25°} = -67.8°$ (0.1 M NaOH, c=0.4). The mass spectrum showed a molecular ion at 502 m/e for the disilylated species. 'H NMR (200 MHz, CD$_3$OD) δ0.92 (d, J=6 Hz, 6H), 1.37 (m, 2H), 1.60 (m, 1H), 1.78-2.28 (m, 8H), 3.32 (m, 2H), 3.72 (t, J=6 Hz, 1H), 4.13 (d, J=9 Hz, 1H), 5.16 (d, J=9 Hz, 1H), 5.26 (dd, J=6 Hz, J=3 Hz, 1H).

Anal. Calcd. for $C_{16}H_{26}N_2O_5S \cdot \frac{1}{4}H_2O$: C, 52.95; H, 7.36; N, 7.72; S, 8.83. Found: C, 53.00; H, 7.30; N, 7.81; S, 8.53.

EXAMPLE 32

[3R-[3α,6α(S*R*),9aβ]]-6-[[1-Carboxy-3-(4-chlorophenyl)propyl]amino]octahydro-5-oxothiazolo[3,2-a]azepine-3-carboxylic acid

[3R-(3α,6α,9aβ)]-6-Aminooctahydro-5-oxothiazolo[3,2-a]azepine-3-carboxylic acid (100 mg) and 4-(4-chlorophenyl)-2-oxo-butyric acid (0.692 g) were suspended in 2 ml of water and adjusted to pH 6.1 with 1 M NaOH. Sodium cyanoborohydride (82 mg) in 2 ml of water was slowly added via a syringe pump. When reaction was completed, the mixture was absorbed on strong acid ion-exchange resin and eluted with MeOH:H$_2$O (1:1), H$_2$O, and then with 3% pyridine in water. The appropriate fractions were concentrated and dried to yield the product, wt. 142 mg. The material was purified by chromatography on Sephadex LH-20 (MeOH) to afford 122 mg of the diastereomeric mixture. Tlc on silica [1:1:1:1 ethyl acetate:n-butanol:water:acetic acid] indicated two spots, R$_f$=0.76 and R$_f$=0.72 for the two diastereomers. The mass spectrum showed a molecular ion at 453 for the disilylated species minus-COOTMS. 'H NMR (200 MHz, d$_6$-DMSO) δ1.40-2.26 (8H), 2.63 (m, 2H), 3.19 (m, 2H), 3.48 (m, 1H), 3.80 (m, 1H), 5.04 (m, 1H), 5.14 (m, 1H), 7.31 (m, 4H).

EXAMPLE 33

[3R-[3α,6α(S*R*),9aβ]]-6-[[1-(Ethoxycarbonyl)-3-(methylthio)propyl]amino]octahydro-5-oxothiazolo[3,2-a]azepine-3-carboxylic acid To a solution of [3R-(3α,6α,9aβ)]-6-aminooctahydro-5-oxothiazolo[3,2-a]azepine-3-carboxylic acid (0.147 g) and ethyl 4-(methylthio)-2-oxobutyrate (0.564 g) in absolute ethanol (10 ml), powdered 3 A molecular sieves (1.7 g) were added. To this mixture, a solution of sodium cyanoborohydride (0.121 g) in ethanol (2 ml) was slowly added via a syringe pump. When the reaction was completed, the mixture was filtered and the filtrate concentrated. The residue was partitioned between water (20 ml) and ether (20 ml) and the layers separated. The aqueous layer was acidified with 1 M H$_3$PO$_4$ to pH 4.3 and then repeatedly extracted with chloroform. The chloroform layers were dried and then concentrated to give impure product, wt. 0.249 g. Separation of diastereomers was achieved on a Sephadex LH-20 column (MeOH).

The first diastereomer eluted from the column was the (S*) isomer: wt. 0.067 g. Tlc on silica [3:1:1:1 ethyl acetate:n-butanol:water:acetic acid] indicated a single spot, R$_f$=0.70. 'H NMR (200 MHz, CDCl$_3$) δ1.29 (t, J=7 Hz, 3H), 1.59-2.18 (m, 8H), 2.10 (s, 3H), 2.63 (t, J=7 Hz, 2H), 3.18 (m, 1H), 3.37 (m, 1H), 3.50 (t, J=5.5 Hz, 2H), 4.22 (m, 2H), 4.82 (br s, 2H, exchangeable), 4.98 (d, J=6 Hz, 1H), 5.22 (dd, J=6 Hz, J=2 Hz, 1H).

The second diastereomer to elute from the column was the (R*) isomer: wt. 0.065 g. Tlc on silica also indicated a single spot R$_f$=0.71. 'H NMR (200 MHz, CDCl$_3$) δ1.28 (t, J=7.5 Hz, 3H), 1.54-2.16 (m, 8H), 2.12 (s, 3H), 2.66 (m, 2H), 3.08-3.56 (m, 4H), 4.10 (br S, 2H, exchangeable), 4.20 (m, 2H), 4.92 (m, 1H), 5.29 (d, J=5 Hz, 1H).

EXAMPLE 34

[3R-[3α,6α(S*),9aβ]]-6-[[1-Carboxy-3-(methylthio)propyl]amino]octahydro-5-oxothiazolo[3,2-a]azepine-3-carboxylic acid

[3R-[3α,6α(S*),9aβ]]-6-[[1-(Ethoxycarbonyl)-3-(methylthio)propyl]amino]octahydro-5-oxothiazolo[3,2-a]azepine-3-carboxylic acid (60 mg) was dissolved in methanol (0.8 ml) and treated with 0.80 ml of 1 M NaOH solution. After standing overnight, the reaction mixture was absorbed on strong acid ion-exchange resin and eluted with 3% pyridine in water. Concentration of the appropriate fractions yielded the title compound, wt. 56 mg; $[\alpha]_D^{25°} = -94.1°$ (0.1 M NaOH, c=0.37). The mass spectrum showed a molecular ion at 506 m/e for the disilylated species. 'H NMR (200 MHz, CD$_3$OD) δ1.74-2.32 (m, 8H), 2.12 (s, 3H), 2.70 (t, J=8 Hz, 2H), 3.30 (m, 2H), 3.70 (t, J=6 Hz, 1H), 4.24 (d, J=10 Hz, 1H), 5.18 (m, 2H). HPLC analysis (reverse phase) showed a single peak.

Anal. Calcd. for $C_{14}H_{22}N_2O_5S_2$: C, 46.39; H, 6.12; N, 7.73. Found: C, 46.81; H, 6.26; N, 7.87.

EXAMPLE 35

[3R-[3α,6α(R*),9aβ]]-6-[[1-Carboxy-3-(methylthio)-propyl]amino]octahydro-5-oxothiazolo[3,2-a]azepine-3-carboxylic acid

[3R-[3α,6α(R*),9aβ]]-6-[[1-(Ethoxycarbonyl)-3-(methylthio)propyl]amino]octahydro-5-oxothiazolo[3,2-a]azepine-3-carboxylic acid (64 mg) was dissolved in methanol (0.8 ml) and treated with 0.8 ml of 1 M NaOH solution. After standing overnight, the reaction mixture was absorbed on strong acid ion-exchange resin and eluted with 3% pyridine in water. The appropriate fraction was concentrated and dried to give the product, wt. 42 mg; $[\alpha]_D^{25°} = -66.4°$ (0.1 N NaOH, c=0.26). The mass spectrum showed a (M+1) ion at 507 m/e for the disilylated species. HPLC analysis indicated a single component. $^1$H NMR (200 MHz, CD$_3$OD) δ1.72–2.30 (m, 8H), 2.12 (s, 3H), 2.68 (t, J=6 Hz, 2H), 3.30 (m, 2H), 3.84 (t, J=7 Hz, 1H), 4.15 (d, J=9 Hz, 1H), 5.16 (d, J=8 Hz, 1H), 5.24 (dd, J=6 Hz, J=3 Hz, 1H).

Anal. Calcd. for C$_{14}$H$_{22}$N$_2$O$_5$S$_2$: C, 46.39; H, 6.12; N, 7.73. Found: C, 46.22; H, 6.09; N, 7.67.

EXAMPLE 36

[3R-[3α,6α(S*R*),9aβ]]-6-[[1-(Benzyloxycarbonyl)-5-phthalimidopentyl]amino]octahydro-5-oxothiazolo[3,2-a]azepine-3-carboxylic acid A solution of [3R-(3α,6α,9aβ)]-6-aminooctahydro-5-oxothiazolo[3,2-a]azepine-3-carboxylic acid (159 mg) in 10 ml of water was adjusted to pH 6.65 with dilute NaOH solution. The solution was freeze-dried. This residue and benzyl 2-oxo-6-phthalimidohexanoate [1.26 g, prepared by alkylation of benzyl 1,3-dithiane-2-carboxylate with 4-phthalimidobutyl bromide and subsequent oxidative conversion to the ketone with N-bromosuccinimide] were partly dissolved in 30 ml of absolute ethanol. Powdered 3 A molecular sieves (1.7 g) were added. To this mixture, a solution of sodium cyanoborohydride (130 mg) in 3 ml of ethanol was added slowly via a syringe pump. When the reaction had proceeded to completion, the mixture was filtered and the filtrate concentrated. The residue was partitioned between water (50 ml) and ether (25 ml). The layers were separated and the aqueous layer was absorbed on strong acid ion-exchange resin. Elution with water and then 4% pyridine in water permitted the recovery of the product as a mixture of diastereomers, wt. 371 mg. Diastereomers were separated by chromatography on Sephadex LH-20 (MeOH).

The first diastereomer to elute from the column was the (S*) isomer, wt. 135 mg. The mass spectrum showed a molecular ion at 579 m/e. HPLC analysis (reverse phase) indicated a single diastereomer; $^1$H NMR (60 MHz; CD$_3$OD) δ1.18–2.48 (br m, 12H), 3.18 (br s, 2H), 3.62 (br m, 4H), 5.05 (br s, 2H), 5.21 (s, 2H) 7.35 (s, 5H), 7.78 (s, 4H).

The second diastereomer to come off the column was the (R*) isomer, wt. 78 mg. HPLC analysis (reverse phase) indicated a single diastereomer. The mass spectrum showed a molecular ion at 579 m/e. $^1$H NMR (60 MHz, CD$_3$OD) δ1.23–2.18 (m, 12H), 3.08–3.85 (m, 6H), 4.93 (m, 2H), 5.12 (s, 2H), 7.30 (s, 5H), 7.78 (s, 4H).

EXAMPLE 37

[3R-[3α,6α(S*),9aβ]]-6-[(1-Carboxy-5-aminopentyl)amino]octahydro-5-oxothiazolo[3,2-a]azepine-3-carboxylic acid The reductive alkylation product, [3R-[3α,6α(S*),9aβ]]-6-[[1-(benzyloxycarbonyl)-5-phthalimidopentyl]amino]octahydro-5-oxothiazolo[3,2-a]azepine-3-carboxylic acid (135 mg), in 10 ml of methanol was hydrogenated in the presence of glacial acetic acid (0.012 ml) at 40 psi over 10% palladium on carbon (140 mg). When the deblocking was completed, the catalyst was removed by filtration and the filtrate concentrated. The product, [3R-[3α,6α(S*),9aβ]]-6-[(1-carboxy-5-phthalimidopentyl)amino]octahydro-5-oxothiazolo[3,2-a]azepine-3-carboxylic acid (84 mg), had the expected spectral properties. A solution of this material in 0.75 ml of methanol was treated with hydrazine hydrate (0.15 ml) and then heated at reflux overnight. The precipitated phthalhydrazide was collected and the filtrate taken to dryness. The residue was absorbed on strong acid ion-exchange resin. Elution with water and then 4% pyridine in water afforded a product (43 mg) which was chromatographed on Sephadex LH-20 (MeOH). The title compound (18 mg) was obtained as a white, hygroscopic solid. Tlc on silica [1:1:1:1 ethyl acetate:n-butanol:water:acetic acid] indicated a single spot, R$_f$=0.40. The mass spectrum (Field Desorption) showed a (M+1) molecular ion at 360 m/e $^1$H NMR (200 MHz, D$_2$O) δ1.46–2.38 (m, 12H), 3.08 (t, J=7 Hz, 2H), 3.18 (d, J=5 Hz, 2H), 3.68 (t, J=7 Hz, 1H), 4.20 (d, J=9 Hz, 1H), 4.97 (m, 1H), 5.19 (m, 1H).

EXAMPLE 38

[3R-[3α,6α(R*), 9aβ]]-6-[(1-Carboxy-5-aminopentyl)amino]octahydro-5-oxothiazolo[3,2-a]azepine-3-carboxylic acid The protected diastereomer, [3R-[3α,6α(R*), 9aβ]]-6-[[1-(benzyloxycarbonyl)-5-phthalimidopentyl]amino]octahydro-5-oxothiazolo[3,2-a]azepine-3-carboxylic acid (78 mg), in methanol (10 ml) was hydrogenated at 40 psi over 10% palladium on carbon (80 mg). When the reaction was completed (occasionally, the reaction mixture required recycling), the catalyst was removed and the filtrate taken to dryness. The product, [3R-[3α,6α(R*),9aβ]]-6-[(1-carboxy-5-phthalimidopentyl)amino]octahydro-5-oxothiazolo[3,2-a]azepine-3-carboxylic acid (29 mg), had the expected spectral properties. A solution of this material in methanol (1.5 ml) was treated with hydrazine hydrate (0.05 ml) and heated at reflux overnight. The precipitate was collected and the filtrate concentrated under reduced pressure. The residue was dried under vacuum to remove excess hydrazine and then absorbed on strong acid ion-exchange resin. Elution with water and then 4% pyridine in water permitted recovery of product (13 mg). Chromatography on Sephadex LH-20 (MeOH) afforded the desired product (3.4 mg). Tlc on silica [1:1:1:1 ethyl acetate:n-butanol:water:acetic acid] indicated a single spot, R$_f$=0.24. $^1$H NMR (200 MHz, D$_2$O) δ1.36–2.40 (m, 12H), 3.04 (t, J=8 Hz, 2H), 3.26 (d, J=4 Hz, 2H), 3.78 (m, 1H), 4.02 (d, J=9 Hz, 1H), 4.96 (m, 1H), 5.11 (m, 1H).

EXAMPLE 39

Methyl [3R-(3α,6α,9aα)]-6-aminooctahydro-5-oxothiazolo[3,2-a]azepine-3-carboxylate Methyl [3R-(3α,6α,9aα]-6-phthalimidooctahydro-5-oxothiazolo[3,2-a]azepine-3-carboxylate (1.25 g) was dissolved in 80 ml of absolute ethanol with gentle heating. Hydrazine hydrate (0.178 ml) was added and the mixture stirred at room temperature for 4 days under nitrogen. The reaction mixture was concentrated and the residue dried under vacuum to remove trace amounts of hydrazine. The residue was treated with 0.5 M HCl (85 ml) at 0° for 3 hours. The precipitated phthalhydrazide (495 mg) was collected. The filtrate was neutralized with 1 M NaOH to pH 10.0 and extracted with $CH_2Cl_2$. Concentration afforded the amino ester, 0.8 g. Exact mass measurement: obs., 244.0880; calcd., 244.0881. $^1$H NMR (200 MHz, $CDCl_3$) 1.58 (br s, 2H, $NH_2$), 1.66-2.20 (br m, 6H), 3.11 (½ABq, $J_{AB}=13$ Hz, $\Delta V_{AB}=35$, $J_{AX}=4$ Hz, 1H), 3.29 (½ABq, $J_{AB}=13$ Hz, $\Delta V_{AB}=35$, $J_{BX}=7$ Hz, 1H), 3.76 (s, 3H), 3.87 (m, 1H), 5.23 (dd, J=7 Hz, J=4 Hz, 1H), 5.55 (d, J=10 Hz, 1H).

EXAMPLE 40

[3R-(3α,6α,9aα)]-6-Aminooctahydro-5-oxothiazolo[3,2-a]azepine-3-carboxylic acid Methyl [3R-(3α,6α,9aα)]-6-aminooctahydro-5-oxothiazolo[3,2-a]azepine-3-carboxylate (0.8 g) was dissolved in 15 ml of methanol and treated with 13.5 ml of 1 M NaOH solution. The reaction mixture was stirred overnight at room temperature under nitrogen and then absorbed on strong acid ion-exchange resin. Elution with 3% pyridine in water permitted the recovery of the product, 653 mg. Tlc on silica [1:1:1:1 ethyl acetate:n-butanol:water:acetic acid] indicated a single component, $R_f=0.65$. Exact mass measurement, obs. 230.0727; calcd. 230.0725. $^1$H NMR (200 MHz, $D_2O$) δ1.94-2.62 (m, 6H), 3.19 (½ABq, $J_{AB}=12$ Hz, $\Delta V_{AB}=57$, $J_{AX}=8$ Hz, 1H), 3.45 (½ABq, $J_{AB}=12$ Hz, $\Delta V_{AB}=57$, $J_{BX}=7$ Hz, 1H), 4.39 (d, J=11 Hz, 1H), 4.96 (m, 1H), 5.21 (d, J=9 Hz, 1H).

EXAMPLE 41

Methyl [3R-[3α,6α(S*R*),9aα]]-6-[[1-(methoxycarbonyl)-3-phenylpropyl]amino]octahydro-5-oxothiazolo[3,2-a]azepine-3-carboxylate A solution of methyl [3R-(3α,6α,9aα)]-6-aminooctahydro-5-oxothiazolo[3,2-a]azepine-3-carboxylate hydrochloride (152 mg) in aqueous methanol (10 ml, 1:1) was adjusted to pH 6.2 with 0.5 M NaOH solution. The solution was concentrated and then redissolved in absolute methanol (10 ml). Methyl 2-oxo-4-phenylbutyrate (0.78 g) and powdered 3 A molecular sieves (1.5 g) were added. A solution of sodium cyanoborohydride (102 mg) in methanol (3.5 ml) was slowly added via a syringe pump. When the reaction was completed, the sieves were removed by filtration and the filtrate concentrated. The residue was partitioned between $CH_2Cl_2$ (50 ml) and water (50 ml). The $CH_2Cl_2$ layer was dried and then concentrated to dryness. The diastereomers were separated by silica gel chromatography with 1:1 hexane:ethyl acetate as eluant.

The first diastereomer ($R_f=0.35$) eluted from the column was methyl [3R-[3α,6α(R*), 9aα]]-6-[[1-(methoxycarbonyl)-3-phenylpropyl]amino]octahydro-5-oxothiazolo[3,2-a]azepine-3-carboxylate, wt. 78 mg. $^1$H NMR (200 MHz, $CDCl_3$) δ1.53-2.22 (m, 8H), 2.72 (t, J=8 Hz, 2H), 3.12 (m, 1H), 3.28 (m, 1H), 3.54 (m, 1H), 3.66 (m, 1H), 3.76 (s, 6H), 5.24 (dd, J==7 Hz, J=3 Hz, 1H), 5.70 (d, J=10 Hz, 1H), 7.28 (m, 5H); exact mass measurement, obs. 420.1685, calcd. 420.1718.

Anal. Calcd. for $C_{21}H_{28}N_2O_5S$: C, 59.98; H, 6.71; N, 6.66; S, 7.63. Found: C, 60.05; H, 6.93; N, 6.52; S, 7.79.

The second diastereomer ($R_f=0.26$) to come off the column was methyl [3R-[3α,6α(S*), 9aα]]-6-[[1-(methoxycarbonyl)-3-phenylpropyl]amino]octahydro-5-oxothiazolo[3,2-a]azepine-3-carboxylate wt. 120 mg. This isomer was recrystallized from ether-petroleum ether (1:1), m.p. 123.5°-24°. $^1$H NMR (200 MHz, $CDCl_3$) δ1.60-2.23 (m, 8H), 2.84 (m, 2H), 3.14 (m, 1H), 3.30 (m, 1H), 3.63 (m, 2H), 3.74 (s, 3H), 3.76 (s, 3H), 5.24 (dd, J=7 Hz, J=3 Hz, 1H), 5.97 (d, J=10 Hz, 1H), 7.28 (m, 5H); exact mass measurement, obs. 420.1725, calcd. 420.1718.

Anal. Calcd. for $C_{21}H_{28}N_2O_5S$: C, 59.98; H, 6.71; N, 6.66; S, 7.63. Found: C, 60.12; H, 6.77; N, 6.46; S, 7.93.

EXAMPLE 42

[3R-[3α,6α(S*),9aα]]-6-[(1-Carboxy-3-phenylpropyl)amino]octahydro-5-oxothiazolo[3,2-a]azepine-3-carboxylic acid Methyl [3R-[3α,6α(S*),9aα]]-6-[[1-(methoxycarbonyl)-3-phenylpropyl]amino]octahydro-5-oxothiazolo[3,2-a]azepine-3-carboxylate (125 mg) was dissolved in 1 ml of MeOH and 2 ml of 1 M NaOH solution (gentle heating was required). After standing overnight at room temperature, the reaction mixture was absorbed on strong acid ion-exchange resin and eluted with 3% pyridine in water. The appropriate fraction was concentrated and dried to afford a white solid, wt. 99 mg. Recrystallized from water-methanol to give fine white needles, wt. 76 mg; m.p. 191.5°-93° (dec); Tlc on silica [1:1:1:1 ethyl acetate:n-butanol:water:acetic acid] indicated a single component, $R_f=0.75$; I.R. (KBr): 1725 and 1622 $cm^{-1}$; $^1$H NMR (200 MHz, $d_6$-DMSO) δ1.42-2.24 (m, 8H), 2.76 (m, 2H), 3.03 (dd, J=12 Hz, J=2.5 Hz, 1H), 3.38 (m, 3H), 4.99 (d, J=5 Hz, 1H), 5.94 (d, J=9 Hz, 1H), 7.26 (m, 5H); $[\alpha]_D^{25°}=-57.7°$ (0.1 M NaOH, c=0.39).

Anal. Calcd. for $C_{19}H_{24}N_2O_5S \cdot H_2O$: C, 55.59; H, 6.39; N, 6.83; S, 7.81. Found: C, 55.56; H, 6.45; N, 6.69; S, 7.90.

EXAMPLE 43

[3R-[3α,6α(R*),9aα]]-6-[(1-Carboxy-3-phenylpropyl)amino]octahydro-5-oxothiazolo[3,2-a]azepine-3-carboxylic acid Methyl [3R-[3α,6α(R*), 9aα]]-6-[[1-(methoxycarbonyl)-3-phenylpropyl]amino]octahydro-5-oxothiazolo[3,2-a]azepine-3-carboxylate (28 mg) was dissolved in 2 ml of methanol and 0.5 ml of 1 M NaOH solution. After standing overnight, the reaction mixture was absorbed on strong acid ion-exchange resin and eluted with 3% pyridine in water. Concentration of the appropriate fraction yielded 26 mg of product. Mass spectrum showed a molecular ion at 536 m/e for the disilylated species. Tlc on silica [1:1:1:1 ethyl acetate:n-butanol:water:acetic acid] indicated a single component, $R_f=0.75$. $^1$H NMR (200 MHz, $d_6$-DMSO) δ1.58 (m 2H), 1.94 (m, 6H), 2.67 (t, J=8 Hz, 2H), 3.04 (dd, J=12 Hz, J=3 Hz, 1H), 3.39 (m, 3H, 4.99 (dd, J=7 Hz, J=3 Hz, 1H), 5.64 (d, J=9 Hz, 1H), 7.28 (m, 5H).

EXAMPLE 44

[3R-[3α,6α(S*R*),9aα]]-6-[[1-(Ethoxycarbonyl)-3-phenyl-propyl]amino]octahydro-5-oxothiazolo[3,2-a]azepine-3-carboxylic acid A solution of [3R-(3α,6α,9aα)]-6-aminooctahydro-5-oxothiazolo[3,2-a]azepine-3-carboxylic acid (0.133 g) in 10 ml of water was adjusted to pH 6.7 with dilute NaOH solution. The solution was then freeze-dried. The residue and ethyl 2-oxo-4-phenylbutyrate (0.596 g) were dissolved in 10 ml of absolute ethanol. Powdered 3 A molecular sieves (1.5 g) were added. To this mixture, a solution of sodium cyanoborohydride (0.109 g) in 2 ml of ethanol was slowly added via a syringe pump. When the reaction was completed, the mixture was filtered and the filtrate concentrated. The residue was partitioned between water (50 ml) and ether (50 ml). The layers were separated and the aqueous phase was absorbed on strong acid ion-exchange resin. Elution with water and then 3% pyridine in water permitted the isolation of the title compound as a mixture of diastereomers, wt. 200 mg. The mass spectrum was consistent with the structure and HPLC analysis (reverse phase) indicated approximately a 60:40 mixture of diastereomers. 'HNMR (200 MHz, CDCl₃) δ1.25 (t, J= 7 Hz, 3H), 1.52–2.20 (m, 8H), 2.74 (m, 2H), 3.23 (m, 2H), 3.54 (m, 2H), 4.18 (m, 2H), 5.22 (m, 1H), 5.64 and 5.92 (d, 1H) 5.82 (br s, 2H, exchangeable), 7.26 (m, 5H). The diastereomers can be separated by chromatography on a reverse phase column.

EXAMPLE 45

Ethyl [3R-[3α,6α(S*R*), 9aα]]-6-[[1-(ethoxycarbonyl)-3-phenylpropyl]amino]octahydro-5-oxothiazolo[3,2-a]azepine-3-carboxylate Anhydrous hydrogen chloride was bubbled through a solution of [3R-[3α,6α(S*R*), 9aα]]-6-[[1-ethoxycarbonyl)-3-phenylpropyl]amino]octahydro-5-oxothiazolo[3,2-a]azepine-3-carboxylic acid in absolute at 0° for 15 minutes. The reaction mixture was stirred at room temperature overnight and then concentrated under reduced pressure. The residue was partitioned between water and ether and then neutralized. The ethereal layer was dried and then taken to dryness to afford an oil as a mixture of diastereomer. The diastereomers can be separated by chromatography. Each diastereomer exhibited the characteristic mass spectra and 'HNMR spectra were consistent with their structures.

EXAMPLE 46

Benzyl [3R-(3α,6α,9aα)]-6-aminooctahydro-5-oxothiazolo[3,2-a]azepine-3-carboxylate

[3R-(3α,6α,9aα)]-6-Aminooctahydro-5-oxothiazolo[3,2-a]azepine-3-carboxylic acid was suspended in benzyl alcohol at 0° and treated with thionyl chloride. The reaction mixture was stirred overnight at room temperature and under an inert atmosphere. Ether was added and the precipitate collected. This material was suspended in water and then neutralized with one equivalent of base to afford, upon extraction, the desired compound. Tlc, mass spectrum, and 'HNMR were consistent with its structure.

EXAMPLE 47

Benzyl [3R-[3α,6α(S*R*),9aα]]-6-[(1-carboxy-3-phenylpropyl)amino]octahydro-5-oxothiazolo[3,2-a]azepine-3-carboxylate Hydrochloride To a solution of benzyl [3R-[3α,6α,9aα)]-6-aminooctahydro-5-oxothiazolo[3,2-a]azepine-3-carboxylate and t-butyl 2-oxo-4-phenylbutyrate in absolute ethanol, powdered 3 A molecular sieves and one equivalent of acetic acid were added. To this mixture, a solution of sodium cyanoborohydride in ethanol was slowly added. When reaction was completed, standard work-up yielded the product, Benzyl [3R-[3α,6α(S*R*), 9aα]]-6-[[1-(tert. butoxycarbonyl)-3-phenylpropyl]amino]octahydro-5-oxothiazolo[3,2-a]azepine-3-carboxylate, as a mixture of diastereomers. Chromatography permitted the separation of the diastereomers and deblocking with 4 N HCl in ether acetate provided the title compounds. Each diastereomers displayed spectra properties consistent with their structures.

EXAMPLE 48

Ethyl [3R-(3α,6α,9aα)]-6-aminooctahydro-5-oxothiazolo[3,2-a]azepine-3-carboxylate

[3R-(3α,6α, 9aα)]-6-Aminooctahydro-5-oxothiazolo[3,2-a]azepine-3-carboxylic acid was dissolved in ethanol at 0° and the solution saturated with anhydrous hydrogen chloride. The reaction mixture was then stirred overnight at room temperature. The mixture was taken to dryness and the residue suspended in water. Neutralization with base and then extraction afforded the title compound.

EXAMPLE 49

Ethyl [3R-[3α,6α(S*R*),9aα]]-6-[(1-carboxy-3-phenylpropyl)amino]octahydro-5-oxothiazolo[3,2-a]azepine-3-carboxylate Hydrochloride To a solution of ethyl [3R-(3α,6α,9aα)]-6-aminooctahydro-5-oxothiazolo[3,2-a]azepine-3-carboxylate and t-butyl 2-oxo-4-phenylbutyrate in absolute ethanol, powdered 3 A molecular sieves and one equivalent of acetic acid were added. To this mixture, a solution of sodium cyanoborohydride in ethanol was slowly added. When the reaction was completed, the sieves were removed by filtration and the filtrate concentrated. The residue was partitioned between water and CH₂Cl₂. Concentration of the CH₂Cl₂ portion afforded the product, ethyl [3R-[3α,6α(S*R*),9aα]]-6-[[1-tert. butoxycarbonyl)-3-phenylpropyl]amino]octahydro-5-oxothiazolo[3,2-a]azepine-3-carboxylate, as a mixture of diastereomers along with excess α-ketoester and α-hydroxy ester. Chromatography on silica permitted the isolation of each diastereomer in high purity. Each diastereomer was deblocked with 4 N HCl in ethyl acetate to give the title compounds which exhibited their expected spectral properties.

EXAMPLE 50

Additional Products of Formula I

Additional keto acids and keto esters listed in Table I below as well as those employed in the foregoing examples can be reductively condensed with intermediates

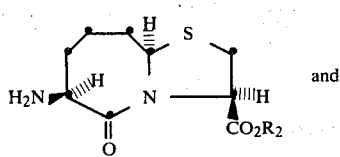
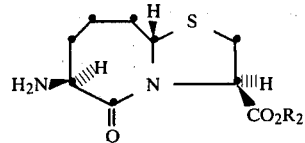

by the methods described hereinabove to yield, after removal of protecting groups, if any, products of Formula I listed below in Table II. In intermediates VIIIa and VIIIb, $R_2$ can be hydrogen, benzyl, phenyl, methyl, ethyl, n-butyl, and allyl groups. The latter ester groups can be introduced by methods analagous with the benzyl ester synthesis or by methods indicated in footnote 5 to Table II. In Table II, the stereochemistry at 9a refers to the hydrogen configuration being R or S at the ring structure in the bicyclic lactam part-structure of Formula I compounds.

TABLE I
KETO ACIDS AND KETO ESTERS OF THE FORMULA: $R_1COCO_2R$
IX

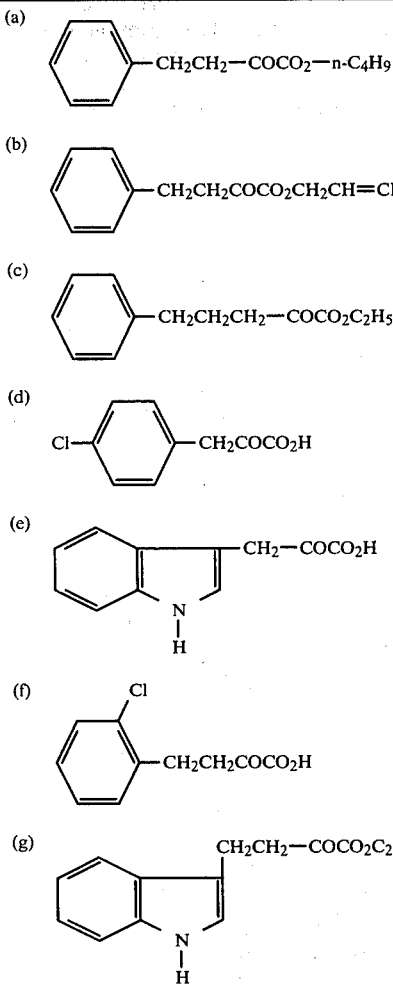
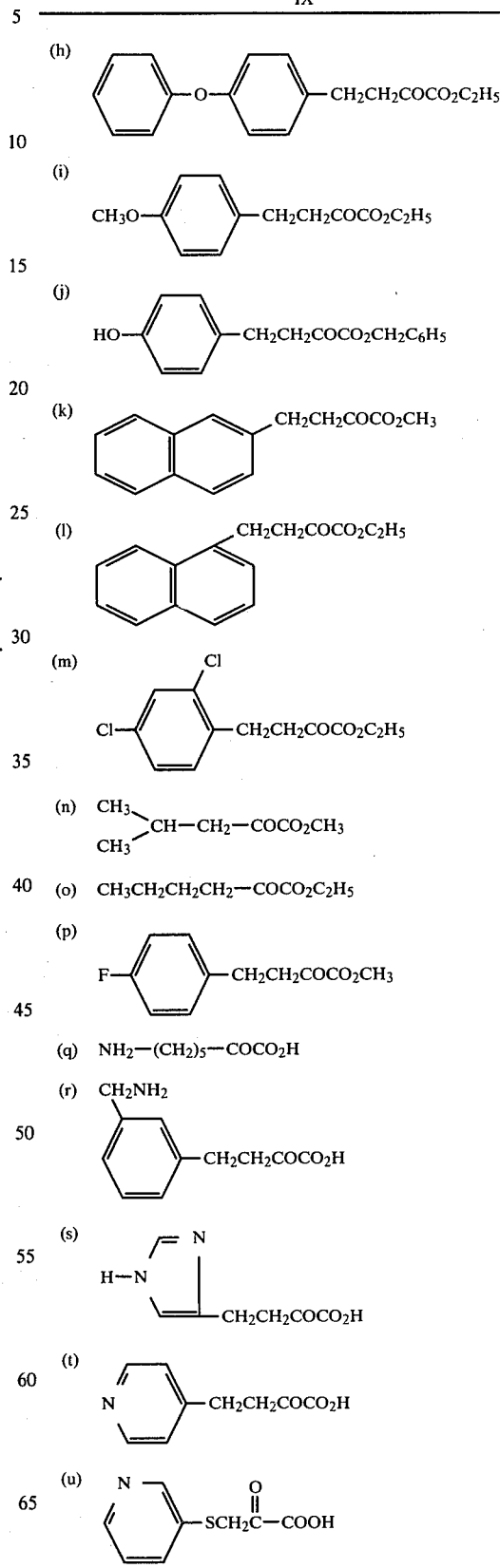

TABLE I-continued
KETO ACIDS AND KETO ESTERS OF THE FORMULA: $R_1COCO_2R$ IX (v) $HOCH_2CH_2-COCO_2C_2H_5$ (3)

(w) $(CH_3)_2N-(CH_2)_4-COCO_2H$ (x) 2-$NO_2$-$C_6H_4$-$CH_2CH_2COCO_2C_2H_5$ (4)

(y) 3-$NO_2$-$C_6H_4$-$CH_2CH_2COCO_2H$ (4)

(z) isoquinolin-4-yl-$CH_2CH_2COCO_2H$ (aa) isoquinolin-1-yl-$CH_2CH_2COCO_2H$ (bb) thien-2-yl-$CH_2CH_2COCO_2C_2H_5$ (cc) quinolin-2-yl-$CH_2CH_2COCO_2H$ (dd) $C_6H_5-OCH_2C(O)-CO_2C_2H_5$ (ee) $C_6H_5-SCH_2C(O)-CO_2H$ (ff) $C_6H_5-CH_2SCH_2C(O)-CO_2C_2H_5$ (1) Protected as the N—phthaloyl derivative.
(2) 2-Imidazole NH protected as the N—benzyl derivative.
(3) Protected as the O—benzyl derivative.
(4) Precursor to m-amino derivative by $H_2/Pd$.

TABLE II
Additional Products of Formula I:

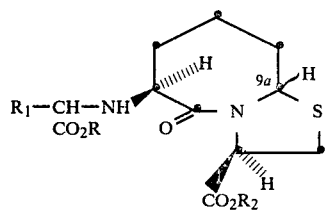

| | R | $R_1$ | $R_2$ | (9a) Stereochemistry |
|---|---|---|---|---|
| (1) | n-$C_4H_9$— | $C_6H_5$-$CH_2CH_2$— | H | S |
| (2) | $CH_2=CH-CH_2$— | $C_6H_5$-$CH_2CH_2$— | $C_2H_5$ | R |
| (3) | $C_2H_5$— | $C_6H_5$-$CH_2CH_2$— | $C_2H_5$— | S |
| (4) | $C_2H_5$— | $C_6H_5$-$CH_2CH_2$— | $CH_2=CH-CH_2$(5) | R |

TABLE II-continued
Additional Products of Formula I:
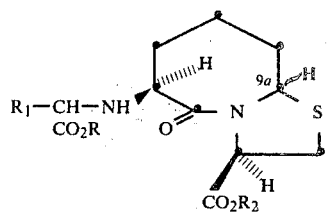
| R | $R_1$ | $R_2$ | (9a) Stereochemistry |
|---|---|---|---|
| (5) Ph–CH$_2$ | Ph–CH$_2$CH$_2$ | H | S |
| (6) CH$_3$– | Ph–CH$_2$CH$_2$ | n-C$_4$H$_9$–(5) | S |
| (7) H– | Ph–CH$_2$CH$_2$ | Ph(5) | R |
| (8) CH$_3$– | Ph–CH$_2$CH$_2$ | n-C$_4$H$_9$(5) | R |
| (9) CH$_3$– | Ph–CH$_2$CH$_2$ | C$_2$H$_5$– | R |
| (10) CH$_3$– | Ph–CH$_2$CH$_2$ | Ph–CH$_2$– | S |
| (11) H | Ph–CH$_2$CH$_2$– | Ph–CH$_2$– | S |
| (12) C$_2$H$_5$– | Ph–CH$_2$CH$_2$CH$_2$ | H | R |
| (13) H | 4-Cl-C$_6$H$_4$–CH$_2$– | H | R |
| (14) H | (3-indolyl)–CH$_2$ | H | R |

TABLE II-continued
Additional Products of Formula I:

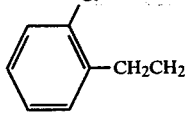

| | | | (9a) |
|---|---|---|---|
| R | $R_1$ | $R_2$ | Stereochemistry |
| (15) H | 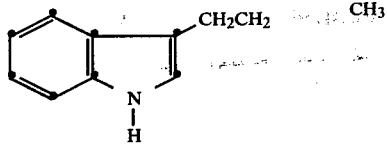 2-Cl-C6H4-CH2CH2 | H | R |
| (16) $C_2H_5$— | 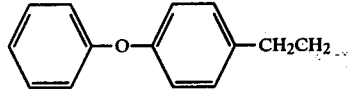 (indol-3-yl)-CH2CH2 | $CH_3$ | R |
| (17) $C_2H_5$— | 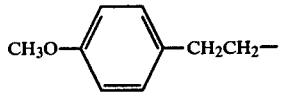 4-PhO-C6H4-CH2CH2 | H | R |
| (18) $C_2H_5$— | $CH_3O$—C6H4—$CH_2CH_2$— | n-$C_4H_9$ | S |
| (19) Ph—$CH_2$— | HO—C6H4—$CH_2CH_2$ | H | R |
| (20) $CH_3$— | (naphth-2-yl)-$CH_2CH_2$ | $C_2H_5$ | S |
| (21) $C_2H_5$ | (naphth-1-yl)-$CH_2CH_2$ | Ph-$CH_2$ | R |
| (22) $C_2H_5$— | $CH_3S$—$CH_2CH_2$— | H | S |
| (23) $CH_3$ | $(CH_3)_2$—$CH$—$CH_2$— | n-$C_4H_9$ | S |
| (24) $C_2H_5$— | $CH_3CH_2CH_2CH_2$ | $C_2H_5$ | R |
| (25) $CH_3$— | 4-F-C6H4-$CH_2CH_2$— | Ph-$CH_2$ | R |
| (26) H | $NH_2(CH_2)_5$— | H | S |
| (27) H | 3-($CH_2NH_2$)-C6H4-$CH_2CH_2$ | H | S |

TABLE II-continued
Additional Products of Formula I:

[Structure: R₁—CH(CO₂R)—NH—C(=O)—[bicyclic ring with N, S, positions labeled H, 9a, H, and CO₂R₂ substituent]]

| R | R₁ | R₂ | (9a) Stereochemistry |
|---|---|---|---|
| (28) H | H—N=CH—N=C(CH₂CH₂—)— (imidazole-CH₂CH₂) | H | S |
| (29) H | 3-pyridyl-S-CH₂— | H | R |
| (30) C₂H₅ | HOCH₂CH₂— | C₂H₅ | R |
| (31) H | (CH₃)₂N—(CH₂)₄— | H | S |
| (32) C₂H₅ | 2,4-dichlorophenyl-CH₂CH₂— | —CH₂ | S |
| (33) H | 3-aminophenyl-CH₂CH₂— | —CH₂— | R |
| (34) H | 4-isoquinolinyl-CH₂CH₂ | H | S |
| (35) H | 4-pyridyl-CH₂CH₂ | H | R |
| (36) C₂H₅ | 2-aminophenyl-CH₂CH₂— | H | S |
| (37) C₂H₅ | 1-isoquinolinyl-CH₂CH₂ | C₂H₅ | S |

TABLE II-continued

Additional Products of Formula I:

| R | R₁ | R₂ | (9a) Stereochemistry |
|---|---|---|---|
| (38) $C_2H_5$ | [thiophene]-$CH_2CH_2$— | $CH_2=CH-CH_2$ | S |
| (39) H | [quinoline]-$CH_2CH_2$ | H | R |
| (40) $C_2H_5$ | [phenyl]-$O-CH_2$ | H | S |
| (41) H | [phenyl]-$S-CH_2$ | H | R |
| (42) $C_2H_5$ | [phenyl]-$CH_2SCH_2$ | H | R |

(5)The required $R_2$ ester can be prepared by first protecting VIII as its t-BOC derivative and then reacting it with DCC and the desired alcohol or phenol in the presence of 4-dimethylamino pyridine. In some examples, the $R_2$ ester can also be introduced by reaction of protected VIII with cesium carbonate and the appropriate alkyl halide in DMF.

EXAMPLE 51

Compressed Tablet containing 5 mg. of active ingredient

| | Per tablet, Mg. |
|---|---|
| [3R—[3α,6α(S*),9aβ]]-6-[(1-carboxy-3-phenylpropyl)amino]octahydro-5-oxothiazolo[3,2-a]azepine-3-carboxylic acid | 5 |
| Calcium phosphate dibasic | 245 |
| Ethyl cellulose (as 5% solution in ethanol) | 5 |
| Unmixed granulation | 255 |
| Add: | |
| Starch, corn | 14 |
| Magnesium stearate | 1 |
| | 270 |

EXAMPLE 52

Dry filled capsule containing 5 mg. of active ingredient of Example 51

| | Per capsule, mg. |
|---|---|
| Lactose | 5 |
| Magnesium stearate | 273 |
| Mixed powders | 2 |
| | 280 |

Mix the active ingredient above, lactose, and magnesium stearate and reduce to a No. 60 mesh powder. Encapsulate, filling 285 mg. in each No. 2 capsule.

EXAMPLE 53

Compressed Tablet containing 5 mg. of active ingredient

| | Per tablet, Mg. |
|---|---|
| [3R—[3α,6α(S*),9aβ]]-6-[[1-(ethoxycarbonyl)-3-phenylpropyl]amino]octahydro-5-oxothiazolo[3,2-a]azepine-3-carboxylic acid | 5 |
| Calcium phosphate dibasic | 245 |
| Ethyl cellulose (as 5% solution in ethanol | 5 |
| Unmixed granulation | 255 |
| Add: | |
| Starch, corn | 14 |
| Magnesium stearate | 1 |
| | 270 |

EXAMPLE 54

Dry filled capsule containing 5 mg. of active ingredient of Example 53.

|  | Per capsule, mg. |
|---|---|
| Lactose | 5 |
| Magnesium stearate | 273 |
| Mixed powders | 2 |
|  | 280 |

Mix the active ingredient above, lactose, and magnesium stearate and reduce to a No. 60 mesh powder. Encapsulate, filling 285 mg. in each No. 2 capsule.

What is claimed is:

1. A compound of the formula:

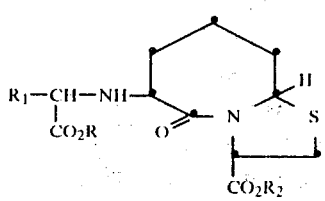

wherein:

R and $R_2$ are independently hydrogen, loweralkyl, aryl, and aryl lower alkyl;

$R_1$ is hydrogen;

alkyl, alkenyl, alkynyl, and unsubstituted cycloalkyl of from 1 to 12 carbon atoms;

substituted lower alkyl wherein the substituent can be halo, hydroxy, carboxy, lower alkylthio, lower alkoxy, lower alkoxy carbonyl, aryl lower alkoxy carbonyl, amino, lower alkylamino, diloweralkylamino, acetylamino, or benzoylamino;

substituted lower alkyl having the formula $R_A(CH_2)_n$—Q—$(CH_2)_m$— wherein n is 0-2, m is 1-3, $R_A$ is aryl or heteroaryl optionally substituted by amino, diloweralkylamino, lower alkylamino, hydroxy, hydroxy loweralkyl, amino lower alkyl, trihaloloweralkyl, cyano, nitro, sulfonamido, benzoyl, 1-naphthoyl, lower alkyl, halo, dihalo, and lower alkoxy, and Q is O, S, N—$R_B$, $CONR_C$, $NR_CCO$, $CH=CH$ wherein $R_B$ is hydrogen, lower alkyl, aryl, aryl lower alkyl, lower alkanoyl, benzoyl, or 1-naphthoyl, and $R_C$ is hydrogen or lower alkyl; aryl;

substituted aryl wherein the substituent is lower alkyl, amino loweralkyl, loweralkoxy, aryloxy, benzoyl, or 1-naphthoyl, hydroxy, halo, or dihalo;

aryl lower alkyl or heteroaryl loweralkyl which include branched lower alkyl groups; substituted aryl lower alkyl or substituted heteroaryl loweralkyl which include branched lower alkyl groups wherein the lower alkyl groups can be substituted by amino, acetylamino, benzoylamino, or hydroxyl and the aryl and heteroaryl groups can be substituted by halo, dihalo, loweralkyl, hydroxy, loweralkoxy, aryloxy, benzoyl, 1-naphthoyl, arylthio, amino, amino lower alkyl, lower alkanoyl amino, benzoylamino, 1-naphthoylamino, diloweralkylamino, lower alkylamino, hydroxy, hydroxy loweralkyl, trihalo loweralkyl, nitro, cyano, or sulfonamido; and, the pharmaceutically acceptable salts thereof, wherein in said R, $R_1$ and $R_2$ groups, the aryl is selected from the group consisting of phenyl, naphthyl, or biphenyl; and, the heteroaryl is selected from the group consisting of indolyl, thienyl, imidazolyl, furyl, benzimidazolyl, pyridyl, quinolinyl, isoquinolinyl, and benzothienyl.

2. A compound of the formula:

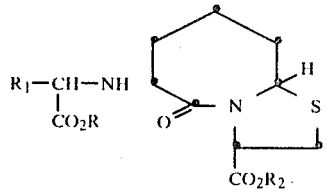

wherein:

R and $R_2$ are hydrogen, loweralkyl, aryl, or aryl lower alkyl;

$R_1$ is alkyl, alkenyl, alkynyl, and unsubstituted cycloalkyl of 1-10 carbon atoms;

substituted lower alkyl wherein the substituent can be hydroxy, lower alkylthio, amino, alkylamino, diloweralkylamino, acetylamino, and benzoylamino;

substituted lower alkyl having the formula $R_A(CH_2)_n$—Q—$(CH_2)_m$— wherein n is 0-2, m is 1-3, $R_A$ is aryl or heteroaryl optionally substituted by alkyl, halo, dihalo, amino, cyano, hydroxy, or alkoxy, and Q is O, S, N—$R_B$, $CONR_C$, $NR_CCO$, or $CH=CH$, wherein $R_B$ is hydrogen, lower alkyl, aryl loweralkyl, lower alkanoyl, benzoyl, or 1-naphthoyl and $R_C$ is hydrogen or lower alkyl;

aryl lower alkyl or heteroaryl loweralkyl which include branched lower alkyl groups;

substituted aryl lower alkyl or substituted heteroaryl loweralkyl which include branched lower alkyl groups wherein the lower alkyl substituents can be amino, acetylamino, benzoylamino, or hydroxy and the aryl and heteroaryl substituents can be lower alkyl, halo, dihalo, amino, cyano, hydroxy, lower alkoxy, amino loweralkyl, or hydroxyloweralkyl; and the pharmaceutically acceptable salts thereof, wherein in said R, $R_1$ and $R_2$ groups, the aryl is selected from the group consisting of phenyl, naphthyl, or biphenyl; and, the heteroaryl is selected from the group consisting of indolyl, thienyl, imidazolyl, furyl, benzimidazolyl, pyridyl, quinolinyl, isoquinolinyl, and benzothienyl.

3. A compound of the formula:

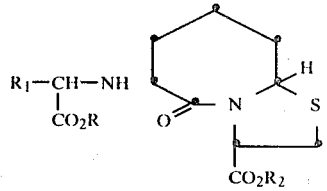

wherein:

R and $R_2$ are independently hydrogen, loweralkyl, aryl, or aryl lower alkyl;

$R_1$ is alkyl of 1-10 carbon atoms which include branched alkyl groups;

substituted lower alkyl wherein the substituent can be amino, acetylamino, benzoylamino, or lower alkylthio;

substituted lower alkyl having the formula $R_A(CH_2)_n$—Q—$(CH_2)_m$— wherein n is 0-1, m is 1-2, $R_A$ is phenyl optionally substituted by halo, dihalo, alkoxy, or cyano, and Q is O or S; aryl lower alkyl or heteroaryl loweralkyl;

substituted aryl lower alkyl or substituted heteroaryl loweralkyl wherein the aryl and heteroaryl substituents are halo, dihalo, cyano, hydroxy, hydroxy lower alkyl, amino, and amino lower alkyl; and, the pharmaceutically acceptable salts thereof, wherein in said R, $R_1$ and $R_2$ groups, the aryl is selected from the group consisting of phenyl, naphthyl, or biphenyl; and, the heteroaryl is selected from the group consisting of indolyl, thienyl, imidazolyl, furyl, benzimidazolyl, pyridyl, quinolinyl, isoquinolinyl, and benzothienyl.

4. A compound of the formula:

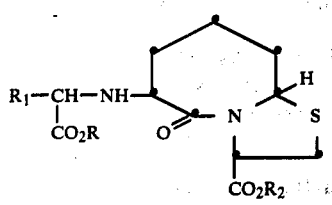

wherein:

R and $R_2$ are independently hydrogen, lower alkyl of 1 to 4 carbon atoms, phenyl, or benzyl; and, $R_1$ is
  alkyl of 1-8 carbon atoms which include branched alkyl groups;
  substituted lower alkyl wherein the substituent can be amino or loweralkylthio;
  substituted lower alkyl having the formula $R_A(CH_2)_n$—Q—$(CH_2)_m$— wherein n is 0, m is 1, $R_A$ is phenyl, and Q is O or S;
  aralkyl wherein the aryl is phenyl or napthyl and the alkyl group contains 1 to 3 carbon atoms, or heteroaralkyl wherein the heteroaryl group is indole, thiophene, imidazole, pyridine, quinoline or isoquinoline and the alkyl group contains 1 to 3 carbon atoms;
  substituted aralkyl wherein the aryl is a phenyl group, the alkyl contains 1 to 3 carbon atoms, and the phenyl substituents can be halo, hydroxy, phenoxy, lower alkoxy, amino, or aminomethyl; and, the pharmaceutically acceptable salts thereof.

5. A compound of claim 4 which has the formula:

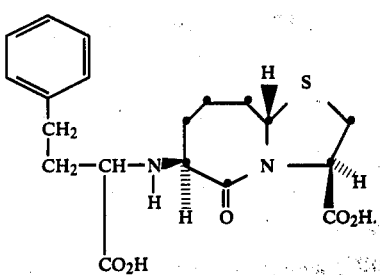

6. A compound of claim 5 which is: [3R-[3α,6α(S*)-,9aα]]-6-[(1-carboxy-3-phenylpropyl)amino]octahydro-5-oxothiazolo[3,2-a]azepine-3-carboxylic acid.

7. A compound of claim 4 which has the formula:

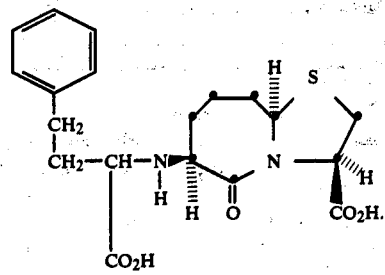

8. A compound of claim 7 which is: [3R-[3α,6α(S*)-,9aβ]]-6-[(1-carboxy-3-phenylpropyl)amino]octahydro-5-oxothiazolo[3,2-a]azepine-3-carboxylic acid.

9. A compound of claim 4 which has the formula:

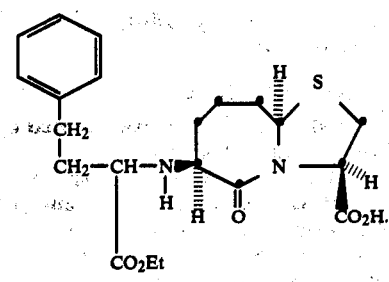

10. A compound of claim 9 which is: [3R-[3α,6α(S*)-,9aβ]]-6-[[1-(ethoxycarbonyl)-3-phenylpropyl]amino]octahydro-5-oxothiazolo[3,2-a]azepine-3-carboxylic acid.

11. A compound of claim 4 which has the formula:

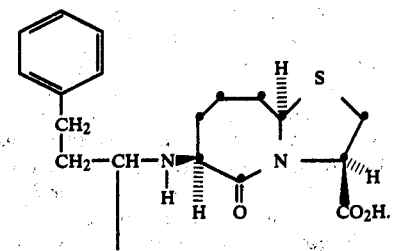

12. A compound of claim 11 which is: [3R-[3α,6α(S*),9aα]]-6-[[1-(ethoxycarbonyl)-3-phenylpropyl]amino]octahydro-5-oxothiazolo[3,2-a]azepine-3-carboxylic acid.

13. A compound of claim 4 which has the formula:

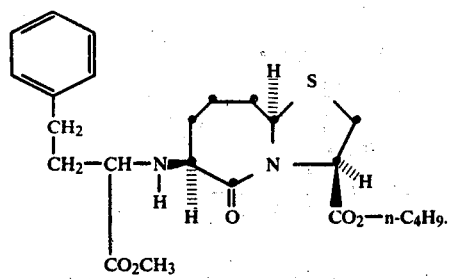

14. A compound of claim 13 which is: n-Butyl [3R-[3α,6α(S*),9aβ]]-6-[[1-(methoxycarbonyl)-3-phenyl-propyl]amino]octahydro-5-oxothiazolo[3,2-a]azepine-3-carboxylate.

15. A compound of claim 4 which has the formula:

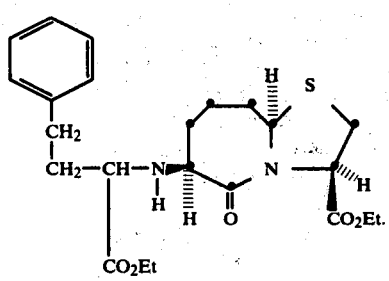

16. A compound of claim 15 which is: Ethyl [3R-[3α,-6α(S*),9aβ]]-6-[[1-(ethoxycarbonyl)3-phenylpropyl]amino]octahydro-5-oxothiazolo[3,2-a]azepine-3-carboxylate.

17. A compound of claim 4 which has the formula:

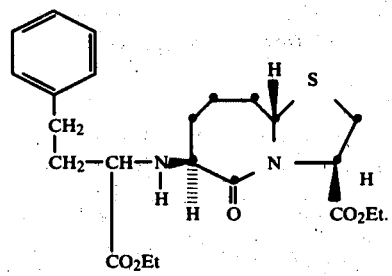

18. A compound of claim 17 which is: Ethyl [3R-[3α,-6α(S*),9aα]]-6-[[1-(ethoxycarbonyl)-3-phenylpropyl]amino]octahydro-5-oxothiazolo[3,2-a]azepine-3-carboxylate.

19. A compound of claim 4 which has the formula:

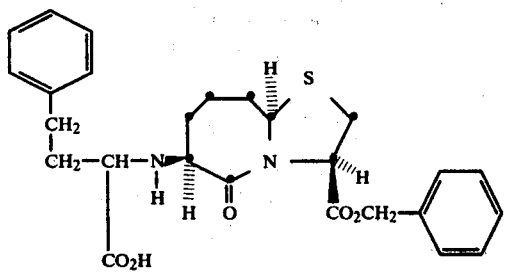

20. A compound of claim 19 which is: Benzyl [3R-[3α,6α(S*),9aβ]]-6-[(1-carboxy-3-phenylpropyl)amino]octahydro-5-oxothiazolo[3,2-a]azepine-3-carboxylate.

21. A compound of claim 4 which has the formula:

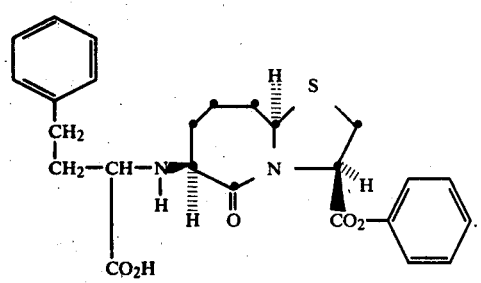

22. A compound of claim 21 which is: Phenyl [3R-[3α,6α(S*),9aβ]]-6-[(1-carboxy-3-phenylpropyl)amino]octahydro-5-oxothiazolo[3,2-a]azepine-3-carboxylate.

23. A compound of claim 4 which has the formula:

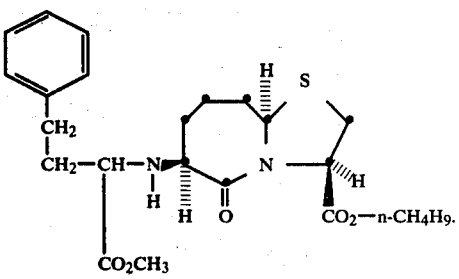

24. A compound of claim 23 which is: n-Butyl [3R-[3α,6α(S*),9aβ]]-6-[[1-(methoxycarbonyl)-3-phenylpropyl]amino]octahydro-5-oxothiazolo[3,2-a]azepine-3-carboxylate.

25. A compound of claim 4 which has the formula:

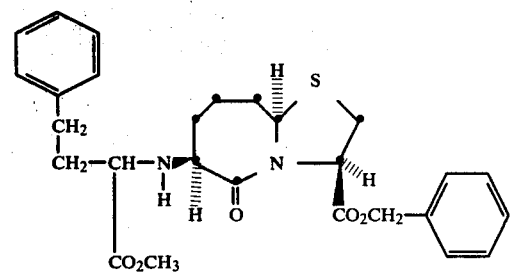

26. A compound of claim 25 which is: Benzyl [3R-[3α,6α(S*),9aβ]]-6-[[1-(methoxycarbonyl)-3-phenylpropyl]amino]octahydro-5-oxothiazolo[3,2-a]azepine-3-carboxylate.

27. A process for producing a compound having the formula:

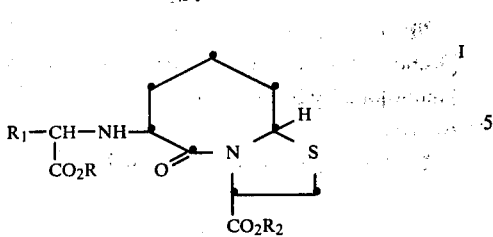

wherein:

R and $R_2$ are independently hydrogen, loweralkyl, aryl, and aryl lower alkyl;

$R_1$ is hydrogen;

alkyl, alkenyl, alkynyl, and unsubstituted cycloalkyl of from 1 to 12 carbon atoms;

substituted lower alkyl wherein the substituent can be halo, hydroxy, carboxy, lower alkylthio, lower alkoxy, lower alkoxy carbonyl, aryl loweralkoxy carbonyl, amino, lower alkylamino, diloweralkylamino, acetylamino, or benzoylamino;

substituted lower alkyl having the formula $R_A(CH_2)_n-Q-(CH_2)_m$ wherein n is 0-2, m is 1-3, $R_A$ is aryl or heteroaryl optionally substituted by amino, diloweralkylamino, lower alkylamino, hydroxy, hydroxy loweralkyl, amino loweralkyl, trihalolow eralkyl, cyano, nitro, sulfonamido, benzoyl, 1-naphthoyl, lower alkyl, halo, dihalo, and lower alkoxy, and Q is O, S, N—$R_B$, $CONR_C$, $NR_CCO$, CH=CH wherein $R_B$ is hydrogen, lower alkyl, aryl, aryl lower alkyl, lower alkanoyl, or benzoyl or 1-naphthoyl, and $R_C$ is hydrogen or lower alkyl;

aryl;

substituted aryl wherein the substituent is lower alkyl, amino loweralkyl, loweralkoxy, aryloxy, benzoyl, 1-naphthoyl, hydroxy, halo, or dihalo; aryl lower alkyl or heteroaryl loweralkyl which include branched lower alkyl groups; substituted aryl lower alkyl or substituted heteroaryl loweralkyl which include branched lower alkyl groups wherein the lower alkyl groups can be substituted by amino, acetylamino, benzoylamino, or hydroxyl and the aryl and heteroaryl groups can be substituted by halo, dihalo, loweralkyl, hydroxy, loweralkoxy, aryloxy, benzoyl, 1-naphthoyl, arylthio, amino, amino lower alkyl, lower alkanoylamino, benzoylamino, 1-naphthoylamino, diloweralkylamino, lower alkylamino, hydroxy, hydroxy loweralkyl, trihalo loweralkyl nitro, cyano, or sulfonamido;

wherein in said R, $R_1$ and $R_2$ groups, the aryl is selected from the group consisting of phenyl, naphthyl, or biphenyl; and, the heteroaryl is selected from the group consisting of indolyl, thienyl, imidazolyl, furyl, benzimidazolyl, pyridyl, quinolinyl, isoquinolinyl, and benzothienyl;

which process comprises:

synthesizing a bicyclic lactam having the formula:

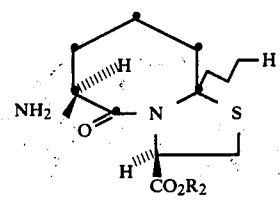

VIII wherein $R_2$ is as defined above, by oxidizing a protected phthalimido derivative (III) to form the aldehyde, 5-formyl-2(S)-phthalimido pentanoic acid (IV); condensing said aldehyde (IV) to form a diastereomeric mixture of thiazolidines (V);

treating said mixture of thiazolidines (V) to effect ring closure thereof and obtain said lactam (VIII); and, subsequently reductively alkylating said lactam with α-keto acids and esters, followed by removal of protecting groups, if any, to yield products of Formula I and, if desired, isolating the biologically more active diastereomer by chromatography or crystallization and, if further desired, preparing a pharmaceutically acceptable salt therefrom by conventional means.

28. A compound having the formula:

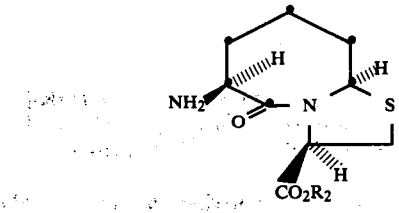

wherein $R_2$ is hydrogen, loweralkyl, aryl, and aralkyl, said alkyl groups having 1-6 carbon atoms and said aryl being selected from the group consisting of phenyl, naphthyl, or biphenyl.

29. A compound having the formula:

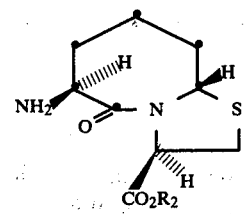

wherein $R_2$ is hydrogen, loweralkyl, aryl, and aralkyl, said alkyl groups having 1-6 carbon atoms and said aryl being selected from the group consisting of phenyl, naphthyl, or biphenyl.

* * * * *